US012551342B2

(12) United States Patent
Shuey et al.

(10) Patent No.: US 12,551,342 B2
(45) **Date of Patent: *Feb. 17, 2026**

(54) DEVICES, SYSTEMS, AND METHODS FOR ADJUSTABLY TENSIONING AN ARTIFICIAL CHORDAE TENDINEAE BETWEEN A LEAFLET AND A PAPILLARY MUSCLE OR HEART WALL

(71) Applicant: BOSTON SCIENTIFIC SCIMED, INC., Maple Grove, MN (US)

(72) Inventors: Daniel Shuey, Pine City, MN (US); Joel T. Eggert, Plymouth, MN (US); Aaron Abbott, Columbia Heights, MN (US); James P. Rohl, Prescott, WI (US); Christopher J. Koudela, New London, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 209 days.

This patent is subject to a terminal disclaimer.

(21) Appl. No.: 18/217,141

(22) Filed: Jun. 30, 2023

(65) Prior Publication Data

US 2023/0338144 A1 Oct. 26, 2023

Related U.S. Application Data

(63) Continuation of application No. 16/919,769, filed on Jul. 2, 2020, now Pat. No. 11,737,875.

(Continued)

(51) Int. Cl.
*A61F 2/24* (2006.01)

(52) U.S. Cl.
CPC .......... *A61F 2/2457* (2013.01); *A61F 2/2466* (2013.01); *A61F 2220/0016* (2013.01)

(58) Field of Classification Search
CPC ............................ A61F 2/2457; A61F 2/2466
See application file for complete search history.

(56) References Cited

U.S. PATENT DOCUMENTS

| | | | |
|---|---|---|---|
| 5,702,397 | A | 12/1997 | Goble et al. |
| 7,736,388 | B2 | 6/2010 | Goldfarb et al. |

(Continued)

FOREIGN PATENT DOCUMENTS

| | | | |
|---|---|---|---|
| EP | 3441045 | A1 | 2/2019 |
| JP | 2018510707 | A | 4/2018 |
| WO | 2016164588 | A1 | 10/2016 |

OTHER PUBLICATIONS

International Search Report and Written Opinion for the International Patent Application No. PCT/US2020/040672, dated Oct. 16, 2020, 14 pages.

(Continued)

*Primary Examiner* — Suba Ganesan
(74) *Attorney, Agent, or Firm* — Seager, Tufte & Wickhem, LLP

(57) ABSTRACT

The present disclosure relates generally to the field of medical devices for delivering artificial chordae tendineae in a patient. A system for adjusting tension in an artificial chordae tendineae includes an artificial chordae tendineae coupleable between a clip and an anchor. The clip is engageable with a leaflet of a heart valve while the anchor is engageable with a papillary muscle or heart wall. The anchor includes a body portion, and a locking portion coupleable with the artificial chordae tendineae and configured to allow movement of the artificial chordae tendineae in a first direction while preventing movement of the artificial chordae tendineae in a second direction opposite the first direction. An actuator is coupled to the locking portion for selectively releasing the locking portion to enable selec- (Continued)

tive movement of the artificial chordae tendineae in the second direction.

15 Claims, 23 Drawing Sheets

Related U.S. Application Data

(60) Provisional application No. 62/873,352, filed on Jul. 12, 2019, provisional application No. 62/870,343, filed on Jul. 3, 2019.

(56) References Cited

U.S. PATENT DOCUMENTS

| | | | | |
|---|---|---|---|---|
| 8,252,050 | B2 | 8/2012 | Maisano et al. | |
| 8,303,622 | B2 | 11/2012 | Alkhatib | |
| 9,681,864 | B1 | 6/2017 | Gammie et al. | |
| 9,872,760 | B2 | 1/2018 | Lopez | |
| 10,136,993 | B1 | 11/2018 | Metchik et al. | |
| 2006/0276890 | A1 | 12/2006 | Solem et al. | |
| 2007/0118151 | A1 | 5/2007 | Davidson | |
| 2007/0276437 | A1 | 11/2007 | Call et al. | |
| 2009/0105729 | A1 | 4/2009 | Zentgraf | |
| 2011/0060407 | A1 | 3/2011 | Ketai et al. | |
| 2011/0301699 | A1 | 12/2011 | Saadat | |
| 2012/0130492 | A1 | 5/2012 | Eggli et al. | |
| 2013/0096611 | A1 | 4/2013 | Sullivan | |
| 2015/0250590 | A1 | 9/2015 | Gries et al. | |
| 2015/0297212 | A1 * | 10/2015 | Reich | A61B 17/3209 606/232 |
| 2017/0245993 | A1 | 8/2017 | Gross et al. | |
| 2017/0252032 | A1 | 9/2017 | Hiorth et al. | |
| 2018/0185153 | A1 | 7/2018 | Bishop et al. | |
| 2018/0250133 | A1 | 9/2018 | Reich et al. | |
| 2018/0303614 | A1 | 10/2018 | Schaffner et al. | |
| 2019/0343633 | A1 * | 11/2019 | Garvin | A61B 17/0401 |
| 2020/0222186 | A1 | 7/2020 | Edmiston et al. | |
| 2021/0000598 | A1 | 1/2021 | Shuey et al. | |
| 2021/0000599 | A1 | 1/2021 | Shuey et al. | |
| 2021/0007847 | A1 | 1/2021 | Eggert et al. | |

OTHER PUBLICATIONS

Author Unknown, Fish Fighter® Kwik-Pull™ Anchor Retriever Fish Fighter Products, 6 pages, retrieved Aug. 29, 2020. URL: https://fishfighterproducts.com/shop/fish-fighter-kwik-pull-anchor-retriever/.

Author Unknown, "Knotless SutureTak® Anchor" Arthrex, 2 pages, retrieved Aug. 29, 2020, 1 page. URL: https://www.arthrex.com/resources/animation/2d7_OmxWw0edpgFLMMbz5A/knotless-suturetak-anchor.

Author Unknown, "Shoulder Labral Repair with Knotless SutureTak® Anchor" Arthrex, retrieved Aug. 29, 2020, URL:https://www.arthrex.com/resources/animation/9cpCPTZLCEGvYQFMdlKwxg/shoulder-labral-repair-with-knotless-suture-anchor 7 pages.

Author Unknown, "Knotless SutureTak Anchor Instability Repair" Arthrex, 2018, 6 pages.

APS—Annapolis Performance Sailing., "Ronstan Constrictor Rope Clutch Expert Review"—YouTube, retrieved Oct. 9, 2020 3 pages.

* cited by examiner

DEVICES, SYSTEMS, AND METHODS FOR ADJUSTABLY TENSIONING AN ARTIFICIAL CHORDAE TENDINEAE BETWEEN A LEAFLET AND A PAPILLARY MUSCLE OR HEART WALL

CROSS-REFERENCE TO RELATED APPLICATIONS

The present application is a continuation of and claims the benefit of the earlier filing date of U.S. patent application Ser. No. 16/919,769, filed Jul. 2, 2020, which claims the benefit of priority under 35 U.S.C. § 119 to U.S. Provisional Patent Application 62/873,352, filed Jul. 12, 2019; and U.S. Provisional Patent Application 62/870,343, filed Jul. 3, 2019, which applications are incorporated herein by reference in their entireties for all purposes.

FIELD

The present disclosure relates generally to the field of medical devices for anchoring to a heart wall. In particular, the present disclosure relates to medical devices, systems and methods for delivering artificial chordae tendineae in a patient.

BACKGROUND

Mitral valve disease is typically repaired via invasive surgical intervention or by complicated pinching of the leaflets together creating dual, smaller openings, or a mitral valve replacement of the native valve. These approaches involve risky by-pass surgery that may include an opening into the patient's chest and heart chamber to expose the mitral valve for direct viewing and repair. Resection, partial removal, and/or repair of the patient's leaflets along with the implantation of a surgical ring are complex techniques used by surgeons to reduce the diameter of the patient's mitral annulus, thus allowing the leaflets to properly coapt and reduce mitral regurgitate flow. Some techniques may slightly reduce regurgitate flow but may not provide a durable solution and do not repair and/or replace damaged chordae tendineae of a valve. Thus, transluminal solutions to mitral valve disease are needed.

A variety of advantageous medical outcomes may be realized by the medical devices, systems, and methods of the present disclosure, which involve anchoring to a heart wall.

SUMMARY

Embodiments of the present disclosure may generally relate to systems and methods for tensioning an artificial chordae tendineae implanted within the heart. In one aspect, a system for adjusting tension in an artificial chordae tendineae includes an artificial chordae tendineae coupleable between a clip and an anchor. The clip may be engageable with a leaflet of a heart valve, while the anchor may be engageable with a papillary muscle or heart wall. The anchor can include a body portion, and a locking portion coupleable with the artificial chordae tendineae and configured to allow movement of the artificial chordae tendineae in a first direction while preventing movement of the artificial chordae tendineae in a second direction opposite the first direction. An actuator may be coupled to the locking portion. The actuator may be operable to selectively release the locking portion to enable selective movement of the artificial chordae tendineae in the second direction.

The anchor may include a housing portion. In some embodiments the body portion, the locking portion and the actuator are disposed in or on the housing portion. The actuator can be couplable to a filament disposed in or on a catheter so that a user can activate the actuator to release the locking portion by applying a force to the filament. The locking portion locks to prevent the artificial chordae tendineae from moving in the second direction when the artificial chordae tendineae applies a force to the locking portion in the second direction.

The locking portion can include a ball or roller for pressing the artificial chordae tendineae between the ball or roller and a surface of the locking portion to prevent the artificial chordae tendineae from moving in the second direction. The actuator may be coupled to the ball or roller to move the ball or roller away from the artificial chordae tendineae to enable the artificial chordae tendineae to move in the second direction. The ball or roller can be movably positioned in a slot having a first wall oriented at an angle "α" with respect to an axis of the artificial chordae tendineae, and a second wall oriented parallel to the axis of the artificial chordae tendineae. Movement of the artificial chordae tendineae in the second direction can tend to press the ball or roller against the artificial chordae tendineae until frictional forces between the artificial chordae tendineae and the first and second surfaces prevents further movement of the artificial chordae tendineae in the second direction.

The system can also include a filament coupled to the ball or roller for enabling a user to manually move the ball or roller in the first direction to reduce the frictional forces between the artificial chordae tendineae, the ball or roller, and the first and second walls of the slot to allow the artificial chordae tendineae to move in the second direction. Moving the artificial chordae tendineae in the first direction may increase tension between the clip and the anchor and moving the artificial chordae tendineae in the second direction can decrease tension between the clip and the anchor.

In some embodiments, the locking portion includes a spring element for coupling to the artificial chordae tendineae to prevent the artificial chordae tendineae from moving in the second direction. In other embodiments, the locking portion includes a clamp for engaging the artificial chordae tendineae. An actuator can be coupled to the clamp for disengaging the clamp from the artificial chordae tendineae. In additional embodiments the locking portion includes a flexible braid member coupled at a first end to an actuator and at a second end to a body portion. The flexible braid member can be disposed within the housing portion while the artificial chordae tendineae can be disposed between the flexible braid member and a sidewall of the housing portion. Thus arranged, when the locking portion is in the locked configuration the flexible braid member can be expanded to press the artificial chordae tendineae against the side wall to prevent the artificial chordae tendineae from moving in the first and second directions. In further embodiments, the locking portion a rotatable locking body having an engagement surface for engaging the artificial chordae tendineae, wherein the rotatable locking body is rotatable to pinch the artificial chordae tendineae between the engagement surface and a body portion of the locking portion to prevent movement of the artificial chordae tendineae.

A device is disclosed for adjusting tension of an artificial chordae tendineae. The device can include an anchor engageable with a papillary muscle or heart wall. The anchor may have a body portion, and a locking portion coupleable with the artificial chordae tendineae and configured to allow movement of the artificial chordae tendineae in a first direction while preventing movement of the artificial chordae tendineae in a second direction opposite the first direction. The device may further include an actuator coupled to the locking portion, where the actuator is configured for selectively releasing the locking portion to enable selective movement of the artificial chordae tendineae in the second direction.

The actuator may be couplable to a filament disposed in or on a catheter so that a user can activate the actuator to release the locking portion by applying a force to the filament. The locking portion may automatically lock to prevent the artificial chordae tendineae from moving in the second direction when the artificial chordae tendineae applies a force to the locking portion in the second direction. In some embodiments, the locking portion comprises a ball or roller for pressing the artificial chordae tendineae between the ball or roller and a surface of the locking portion to prevent the artificial chordae tendineae from moving in the second direction. The actuator can be coupled to the ball or roller to move the ball or roller away from the artificial chordae tendineae to enable the artificial chordae tendineae to move in the second direction.

In some embodiments, the locking portion includes a spring element for coupling to the artificial chordae tendineae to prevent the artificial chordae tendineae from moving in the second direction. In other embodiments, the locking portion includes a clamp for engaging the artificial chordae tendineae. An actuator can be coupled to the clamp for disengaging the clamp from the artificial chordae tendineae.

A method is disclosed for adjusting tension in an artificial chordae tendineae. The method can include disposing an artificial chordae tendineae between a leaflet and a papillary muscle or heart wall, and adjusting a tension in the artificial chordae tendineae by applying a force to the artificial chordae tendineae to move the artificial chordae tendineae from a first position to a second position with respect to an anchor engaged with the papillary muscle or heart wall. A locking portion of the anchor may prevent the artificial chordae tendineae from moving from the second position toward the first position. The method can include visualizing a regurgitation characteristic of a heart valve after the artificial chordae tendineae has been moved from the first position to the second position, and moving the artificial chordae tendineae from the second position to a third position based on said visualization. Moving the artificial chordae tendineae from the second position to the third position may include applying a force to the artificial chordae tendineae. Moving the artificial chordae tendineae from the second position to the third position may include disengaging the locking portion to allow the artificial chordae tendineae to move toward the first position. The method may further include visualizing the regurgitation characteristic of the heart valve after the artificial chordae tendineae has been moved from the second position to the third position, and moving the artificial chordae tendineae from the third position to a fourth position based on said visualization.

BRIEF DESCRIPTION OF THE DRAWINGS

Non-limiting embodiments of the present disclosure are described by way of examples with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
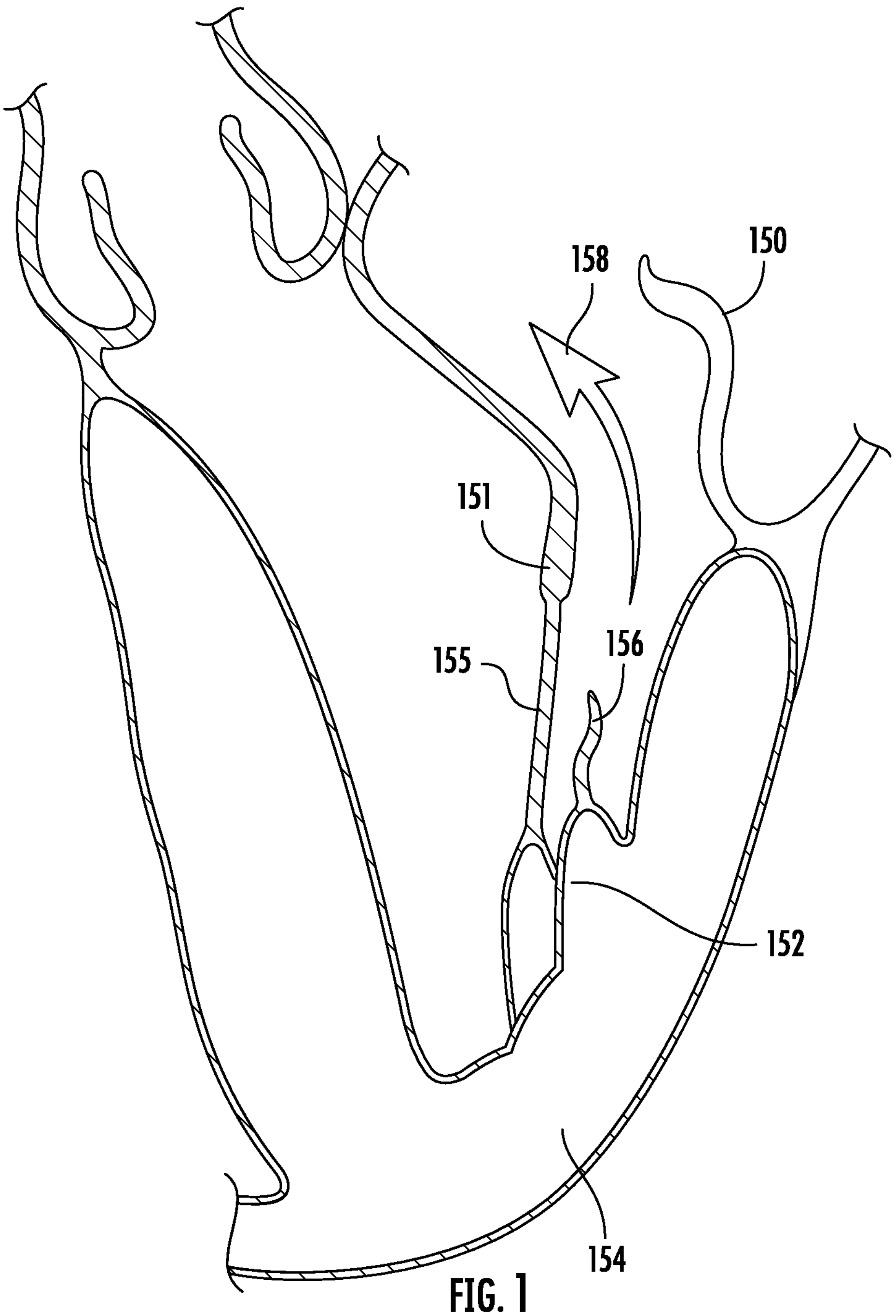
FIG. 1 is a cross-sectional view of flailing leaflet of a mitral valve during blood flow regurgitation.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to medical devices and systems (e.g., transluminal devices inserted through a femoral vein or the like) for selective access to heart tissue, it should be appreciated that such medical devices and systems may be used in a variety of medical procedures that require anchoring to heart tissue. The disclosed medical devices and systems may also be inserted via different access points and approaches, e.g., percutaneously, endoscopically, laparoscopically, or combinations thereof.

As used herein, the singular forms “a,” “an,” and “the” are intended to include the plural forms as well, unless the context clearly indicates otherwise. The terms “comprises” and/or “comprising,” or “includes” and/or “including” when used herein, specify the presence of stated features, regions, steps, elements and/or components, but do not preclude the presence or addition of one or more other features, regions, integers, steps, operations, elements, components and/or groups thereof.

As used herein, “proximal end” refers to the end of a device that lies closest to the medical professional along the device when introducing the device into a patient, and “distal end” refers to the end of a device or object that lies furthest from the medical professional along the device during implantation, positioning, or delivery.

As used herein, the conjunction “and” includes each of the structures, components, features, or the like, which are so conjoined, unless the context clearly indicates otherwise, and the conjunction “or” includes one or the others of the structures, components, features, or the like, which are so conjoined, singly and in any combination and number, unless the context clearly indicates otherwise.

All numeric values are herein assumed to be modified by the term “about,” whether or not explicitly indicated. The term “about,” in the context of numeric values, generally refers to a range of numbers that one of skill in the art would consider equivalent to the recited value (i.e., having the same function or result). In many instances, the term “about” may include numbers that are rounded to the nearest significant figure. Other uses of the term “about” (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to “an embodiment,” “some embodiments,” “other embodiments,” etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Heart disease including atrioventricular heart valve malfunctions impede patient cardiac output, which reduces patient quality of life and lifespan. With reference to the heart 154 illustrated in FIG. 1, as heart disease progresses, the chordae tendineae 155 that connect the papillary muscle or heart wall 152 to a valve leaflet 151 may stretch inelastically and may rupture. A stretched and/or ruptured chordae tendineae 156 may result in a flailing leaflet 150 that may no longer have capacity to form a valving seal for normal heart function. For example, abnormal blood flow regurgitation in the direction of vector 158 may develop. Regurgitation prevents an adequate supply of blood to be delivered through the cardiovascular systems.

Repositioning, repair, and/or replacement of one or more leaflets of a valve and/or chordae tendineae may be desirable to treat heart disease. The devices, systems, and methods of the present disclosure may be used alone or together with other devices, systems, and methods to treat heart disease. Examples of devices, systems, and methods with which embodiments of the present disclosure may be implemented include, but are not limited to, those described in U.S. Patent Application Publication 2021/0007847, titled DEVICES, SYSTEMS, AND METHODS FOR CLAMPING A LEAFLET OF A HEART VALVE, and published Jan. 14, 2021; U.S. Patent Application Publication 2021/0000598, titled DEVICES, SYSTEMS, AND METHODS FOR ANCHORING AN ARTIFICIAL CHORDAE TENDINEAE TO A PAPILLARY MUSCLE OR HEART WALL, and published Jan. 7, 2021; and U.S. Patent Application 2021/0000599, titled DEVICES, SYSTEMS, AND METHODS FOR ARTIFICIAL CHORDAE TENDINEAE, and published Jan. 7, 2021, each of which is herein incorporated by reference in its entirety and for all purposes. Examples of devices described therein may be modified to incorporate embodiments or one or more features of the present disclosure.

Repositioning, repair, and/or replacement of one or more leaflets of a valve and/or chordae tendineae may require one or more devices to be fixed to a leaflet and a portion of heart tissue such as a papillary muscle or heart wall and to couple one or more artificial chordae tendineae therebetween. Embodiment devices described herein may be fixed to a leaflet using a clip, while other embodiment devices may be fixed to a portion of a papillary muscle, heart wall or other heart tissue by engaging an anchor thereto. Such devices may provide fixed points for other devices, systems, or tools to engage in order to manipulate a leaflet of a valve and/or to deliver devices attached to the papillary muscle and/or heart wall.

Devices and minimally invasive methods are disclosed for implanting artificial chordae tendineae in a beating heart with the purpose of repairing a heart valve. In some embodiments a leaflet clip is attached to a heart valve leaflet. The leaflet clip may be connected by an artificial chordae tendineae to an anchor attached to heart tissue such as papillary muscle or heart wall. Tension in the artificial chordae may be adjusted to bring the leaflet clip and the anchor closer or farther apart to minimize regurgitation of blood through the valve.

In some embodiments the artificial chordae can be tensioned from a location adjacent to the proximal end of a catheter. Such tensioning may be performed to decrease the distance between the leaflet clip and the anchor. The anchor continually locks the position of the artificial chordae as the artificial chordae is tensioned. The effect of the artificial chordae tensioning on the leaflet can be observed under medical imaging and further tensioning can be performed until leaflet repair is achieved. If the artificial chordae tendineae is over-tensioned, as evidenced by a visualized regurgitation characteristic of the affected heart valve, the anchor lock can be released by pulling on an actuator and the distance between the leaflet clip and the anchor can be increased to reduce tension in the artificial chordae tendineae. The tension adjustment steps can be repeated. When satisfied with the artificial chordae tendineae tensioning and valve repair, the artificial chordae tendineae is then detached from the catheter and the catheter is removed from the heart. The procedure can then be concluded or additional artificial chordae tendineae can be implanted.

It will be appreciated that one or more aspects of the disclosed devices may be delivered to a leaflet, and heart tissue such as a papillary muscle and/or heart wall, using a catheter or other appropriate delivery device. The catheter may have one or more controls disposed at a proximal end thereof to enable a user to manipulate the disclosed devices using one or more sutures, cables, wires or the like.

As will be appreciated, the specific nature of the delivery device is not critical to the present disclosure as long as the delivery device is configured to allow a user to deliver, implant, and manipulate the disclosed devices at a targeted location within the heart.

It will also be appreciated that delivery, engagement, and manipulation of the disclosed devices may be facilitated by use of known visualization techniques, such as fluoroscopy, ultrasound, intra-cardiac echo, or the like.

Figure 2:
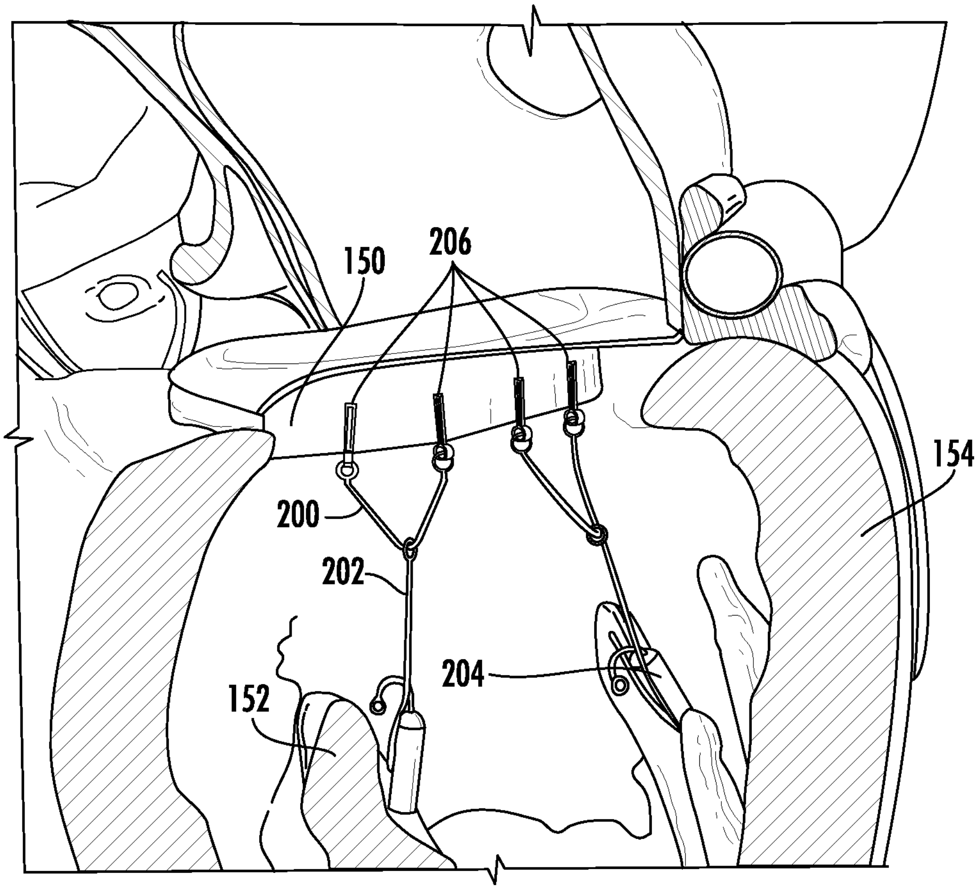
FIG. 2 is a cross-sectional view of a system in which several artificial chordae tendineae are engaged between a heart valve leaflet and a heart wall, according to an embodiment of the present disclosure.

FIG. 2 illustrates an embodiment of a system for connecting one or more filaments 200, 202 between a leaflet 150 of a heart valve and a papillary muscle or heart wall 152 according to the present disclosure. As will be appreciated, the filaments 200, 202 (which serve as artificial chordae tendineae) may comprise sutures made from any of a variety of appropriate materials, a non-limiting example of which includes polytetrafluoroethylene (PTFE). Where the disclosure refers to filaments, it will be appreciated that such filaments comprise artificial chordae tendineae. Anchors 204 may be attached to the papillary muscle or heart wall 152 of a heart 154. Each of the anchors 204 may also be attached to an end of an anchoring filament 202 that serves as an artificial chordae tendineae. The anchoring filaments 202 are attached to a filament 200 that is further attached a plurality of leaflet clips 206 that are coupled to the leaflet 150. A medical professional may adjust the length and tension of the filaments 200 and 202 so that they may replicate and/or replace the natural chordae tendineae of the heart 154 to function with the leaflet 150 of the valve. The medical professional may adjust the tension in the filaments 200, 202 in response to a heart valve regurgitation observation that may be observed via transesophageal echocardiogram, fluoroscopy, or the like. The filaments 200, 202 can be fixed at one end to the leaflet 150 by the leaflet clips 206 and can be fixed at a second end to the papillary muscle or heart wall 152 by the anchor(s) 204. The use of intermediate and/or multiple filaments is contemplated. For example, as shown in the illustrated embodiment a single anchoring filament 202 may be coupled to one or more filaments 200 such that one anchoring filament 202 and one anchor 204 may be used with multiple leaflet clips 206. In some embodiments, the filaments 200 and anchoring filaments 202 may be coupled to one or more leaflet clips 206 and to an anchor 204 during delivery of the system into the heart 154.

Figure 3A:
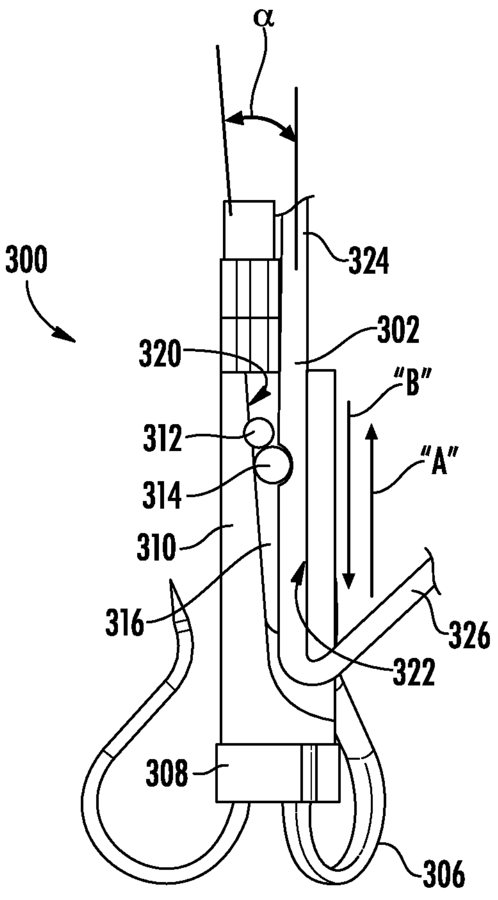
FIGS. 3A and 3B are first and second transparent side views of an artificial chordae tendineae tensioning device according to an embodiment of the present disclosure.
Figure 3B:
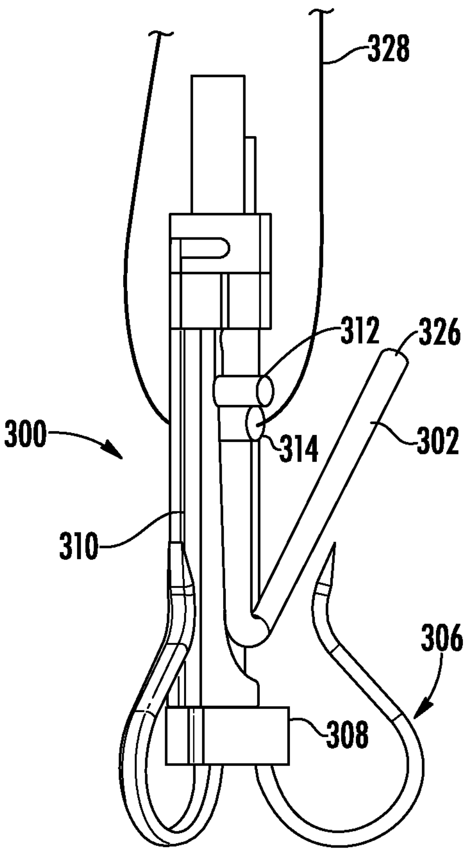
Figure 3C:
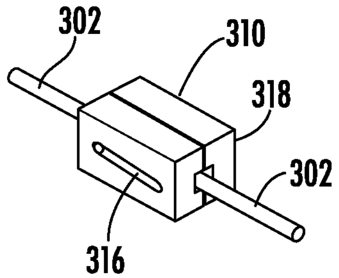
FIG. 3C is an isolated view of a locking portion such as shown in FIGS. 3A and 3B and according to an embodiment of the present disclosure.

With reference now to FIGS. 3A-3C, an embodiment of a device 300 for adjusting the tension of an artificial chordae tendineae 302 according to the present disclosure is illustrated. The device 300 may comprise an anchor having a tissue-engaging portion 306, a body portion 308, and a locking portion 310. As will be described, the locking portion 310 may be couplable to the artificial chordae tendineae 302 to allow the artificial chordae tendineae to move in a first direction (arrow "A") while preventing the artificial chordae tendineae from moving in a second direction (arrow "B") opposite the first direction. In this manner a user can move the artificial chordae tendineae in a direction tending to increase tension thereon (e.g., the first direction), and when the movement is stopped the artificial chordae tendineae will be held in place by the locking portion 310 to thereby maintain the applied tension.

The artificial chordae tendineae is shown in FIGS. 3A, 3B as having a first end 324 and a second end 326. The first end 324 may, in some embodiments, be coupled to a control filament (not shown) that runs through the catheter to a location in which a user can manipulate the tension in the artificial chordae tendineae 302. In some embodiments the first end 324 may include a loop or other connection mechanism through which the control filament may be coupled. Upon completion of the tensioning procedure, the control filament may be detached from the first end 324 and removed via the catheter. The second end 326 of the artificial chordae tendineae 302 may extend within the heart to couple directly or indirectly to one or more leaflet clips 206 (FIG. 2). In some embodiments the second end 326 may couple to a filament 200 (FIG. 2) that, in turn, couples to one or more leaflet clips 206.

In the illustrated embodiment the locking portion 310 comprises a stop member 312 that is fixed, and a roller 314 that is movably positioned in a slot 316 disposed in the locking portion 310 and/or a housing portion 318 surrounding the locking portion. The stop member 312 and the roller 314 are illustrated as being cylindrical in shape, though the shape is not critical and other shapes are contemplated. For example, the stop member 312 may be a protrusion or other surface feature that prevents the roller 314 from continuing to move in the direction of arrow "B" (the second direction) when the roller contacts the stop member. The roller 314 may be provided in other shapes (tapered, curved, etc.), so long as it is movable along the slot 316, as will be described in greater detail. In some embodiments the locking portion 310 is disposed within the housing portion 318. In some embodiments the body portion 308 and the locking portion 310 can be disposed in or on the housing portion 318.

As mentioned, the stop member 312 may be fixed within the locking portion 310 and the roller 314 may be movable within the slot 316. As can be seen, a first wall 320 of the slot 316 may be oriented at an angle "a" with respect to the axis of the artificial chordae tendineae 302, while a second wall 322 of the slot may be oriented parallel to the axis of the artificial chordae tendineae. The roller 314 may contact the artificial chordae tendineae 302 to allow the artificial chordae tendineae to move in the first direction (arrow "A") with respect to the roller 314, and to prevent movement of the artificial chordae tendineae in the second direction (arrow "B").

In use, the stop member 312 may be fixed with respect to the slot 316. The roller 314 and the artificial chordae tendineae 302 can be disposed within the slot 316 such that the roller 314 contacts the artificial chordae tendineae 302. In the illustrated configuration, referred to as the unlocked configuration, the roller 314 presses the artificial chordae tendineae 302 into engagement with a first wall 320 of the locking portion 310, but not to such a degree that it prevents the artificial chordae tendineae from moving in the first direction (arrow "A"). In this configuration, the artificial chordae tendineae 302 can be moved in the first direction (arrow "A") by a user applying a force to a first end 324 of the artificial chordae tendineae to apply tension between the second end 326 of the artificial chordae tendineae and one or more associated leaflet clips 206 (see FIG. 2). The roller 314 may move in the first direction along with the artificial chordae tendineae 302 due to frictional forces between the two, but as mentioned this friction will not prevent the artificial chordae tendineae 302 from moving past the roller 314. Once a target position and/or tension of the artificial chordae tendineae 302 is achieved, the tension in the artificial chordae tendineae may naturally tend to move the artificial chordae tendineae in the second direction (arrow "B"). Friction between the artificial chordae tendineae 302 and the roller 314 will therefore cause the roller 314 to move with the artificial chordae tendineae in the second direction (arrow "B"). Due to the angled nature of the slot 316, however, movement of the roller 314 in the second direction will cause the roller 314 to move toward the artificial chordae tendineae 302, and thus the roller will apply increasing force against the artificial chordae tendineae, which in turn will result in increased friction between the roller, the artificial chordae tendineae, and the second wall 322 of the slot 316. Movement of the roller 314 may continue until the friction between the surfaces prevents the artificial chordae tendineae 302 from moving any further in the second direction (arrow "B").

In some embodiments, movement of the artificial chordae tendineae in the direction of arrow "A" will tend to tighten the artificial chordae tendineae 302 between the device 300 and the leaflet 150 of the heart valve. Where the device 300 is coupled to a papillary muscle or heart wall 152, a tension may be achieved in the artificial chordae tendineae 302 to achieve an effect on regurgitation of blood through the heart valve. Observation of regurgitation may be observed via transesophageal echocardiogram, fluoroscopy, or the like to determine whether an effect on regurgitation has been achieved with the artificial chordae tendineae 302 in place. If, upon observation, the user determines the tension in the artificial chordae tendineae 302 is to be increased, the user may apply additional tension to the artificial chordae tendineae to move it further in the first direction (arrow "A"), followed by additional observation, and so on.

If, upon observation, the user determines the tension in the artificial chordae tendineae 302 is to be decreased, the artificial chordae tendineae may be moved in the second direction (arrow "B"). As described, however, the arrangement of the locking portion may prevent movement of the artificial chordae tendineae 302 in the second direction. Thus, the locking portion 310 may include an actuator 328 configured to manually move the roller 314 in the first direction (arrow "A") to reduce the frictional forces between the artificial chordae tendineae 302, the roller 314 and the second wall 322 of the slot 316 to allow the artificial chordae tendineae 302 to move in the second direction to reduce tension in the artificial chordae tendineae 302 by a target amount. In the illustrated embodiment the actuator 328 is a filament disposed through a central portion of the roller 314. The actuator 328 may run through the catheter to a location in which a user can actuate the actuator to "unlock" the locking portion 310.

Once tension has been reduced, observation of regurgitation may again be observed via transesophageal echocardiogram, fluoroscopy, or the like to determine whether a target affect has been achieved. Additional adjustments of the artificial chordae tendineae 302 in the first and/or second directions can be made until a target effect on heart valve regurgitation is achieved. Upon completion of the tensioning procedure, the actuator 328 may be detached from the roller 314 and removed via the catheter.

Figure 4A:
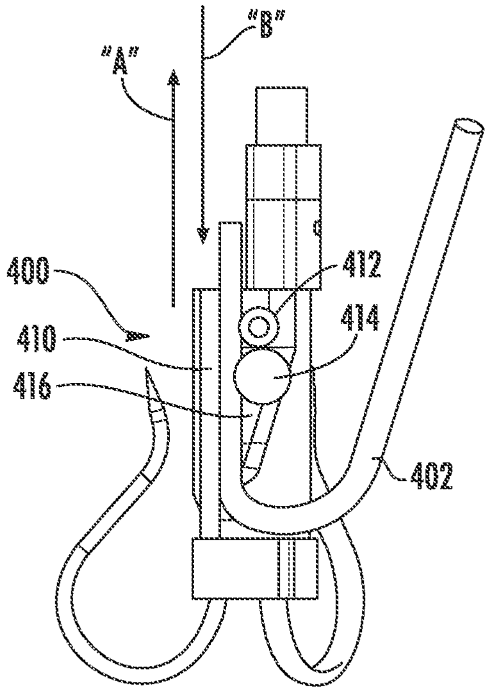
FIGS. 4A and 4B are first and second transparent side views of an artificial chordae tendineae tensioning device according to an embodiment of the present disclosure.
Figure 4B:
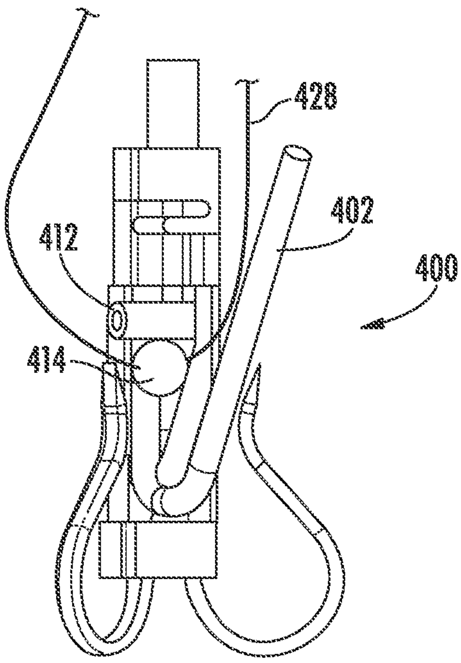

With reference to FIGS. 4A-4B, an embodiment of a device 400 for adjusting the tension of an artificial chordae tendineae 402 according to the present disclosure is illustrated. As will be described, a locking portion 410 may be couplable to the artificial chordae tendineae 402 to allow the artificial chordae tendineae to move in a first direction (arrow "A") while preventing the artificial chordae tendineae from moving in a second direction (arrow "B") opposite the first direction. In this manner a user can move the artificial chordae tendineae 402 in a direction tending to increase tension thereon (e.g., the first direction), and when the movement is stopped the artificial chordae tendineae will be held in place by the locking portion 410 to thereby maintain the applied tension.

The embodiment of FIGS. 4A-4B can be arranged and operates in the same or similar manner to the device 300 of FIGS. 3A-3B, with the exception that in lieu of a roller, the locking portion 410 of device 400 includes a ball member 414 for engaging and locking against the artificial chordae tendineae 402. The remaining elements of the device 400 can be the same as device 300, and are indicated with reference numbers as in FIGS. 3A-3B increased by 100, and operation of the device 400 can be the substantially same, reference being made to the above descriptions of similar elements and operations the sake of simplicity.

Thus, the ball member 414 resides within an angled slot 416 such that it is operable to selectively lock and release the artificial chordae tendineae 402 in the same manner as described in relation to the roller 314. An actuator 428 may be provided through a portion of the ball member 414 and may be operated to manually move the ball member 414 to unlock the locking portion in the same or similar manner to the actuator 328 described previously.

Figure 5A:
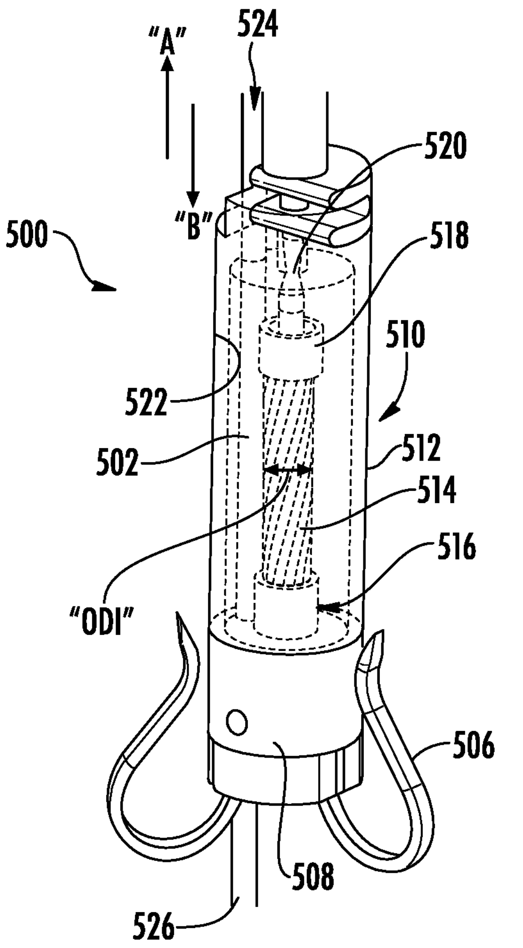
FIGS. 5A and 5B are first and second transparent side views of an artificial chordae tendineae tensioning device according to an embodiment of the present disclosure.
Figure 5B:
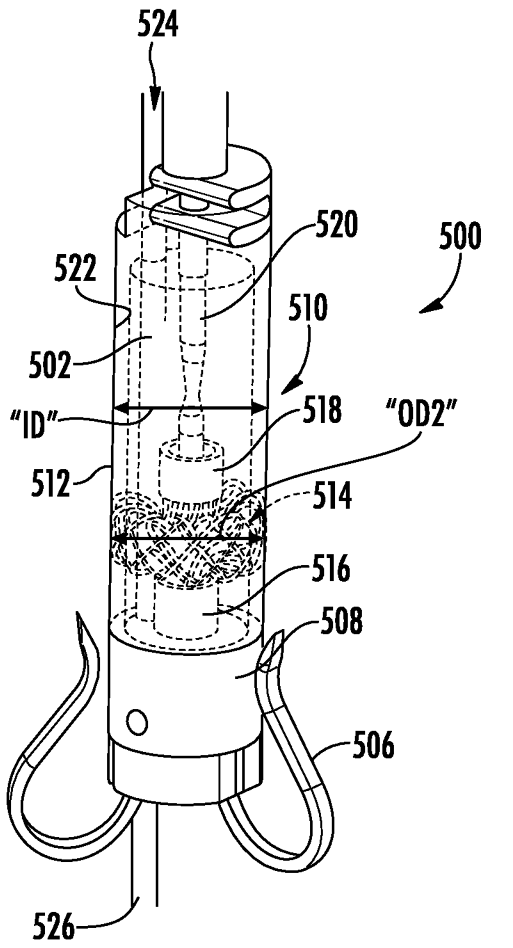

With reference now to FIGS. 5A-5B, an embodiment of a device 500 for adjusting the tension of an artificial chordae tendineae 502 according to the present disclosure is illustrated. The device 500 may comprise an anchor having a tissue-engaging portion 506, a body portion 508, and a locking portion 510. As will be described, the locking portion 510 may be couplable to the artificial chordae tendineae 502 to allow the artificial chordae tendineae to move in a first direction (arrow "A") while preventing the artificial chordae tendineae from moving in a second direction (arrow "B") opposite the first direction. In this manner a user can move the artificial chordae tendineae 502 in a direction tending to increase tension thereon, and when the movement is stopped the artificial chordae tendineae will be held in place by the locking portion 510 to maintain the applied tension.

The artificial chordae tendineae is shown in FIGS. 5A, 5B as having a first end 524 and a second end 526. The first end 524 may, in some embodiments, be coupled to a control filament (not shown) that runs through the catheter to a location in which a user can manipulate the position of (e.g., move) the artificial chordae tendineae 502. In some embodiments the first end 524 may include a loop or other connection mechanism through which the control filament may be coupled. Upon completion of the tensioning procedure, the control filament may be detached from the first end 524 and removed via the catheter. The second end 526 of the artificial chordae tendineae 502 may extend within the heart to couple directly or indirectly to one or more leaflet clips 206 (FIG. 2). In some embodiments the second end 526 may couple to a filament 200 (FIG. 2) that, in turn, couples to one or more leaflet clips 206.

In the illustrated embodiment the locking portion 510 comprises a housing portion 512 within which a portion of the artificial chordae tendineae 502 is disposed. The housing portion 512 may contain a flexible braid member 514 coupled at a first end 518 to an actuator 520 and at a second end 516 to the body portion 508. The flexible braid member 514 may be centrally disposed within the housing portion 512, while the artificial chordae tendineae 502 may be disposed between the flexible braid member 514 and a sidewall 522 of the housing portion 512. In some embodiments the flexible braid member 514 comprises Nitinol. In one example embodiment the flexible braid member 514 has a friction-enhancing coating disposed on at least a portion thereof in order to enhance the frictional engagement between the flexible braid member and the artificial chordae tendineae 502.

The actuator 520 may be movable in the first and second directions (arrows "A" and "B", respectively) to move the flexible braid member 514 between locked and unlocked configurations. When the flexible braid member 514 is in the unlocked configuration, the artificial chordae tendineae can be moved in the first direction (arrow "A") or the second direction (arrow "B"). When the flexible braid member 514 is in the locked configuration, the artificial chordae tendineae can be moved in the first direction (arrow "A") or the second direction (arrow "B"). In some embodiments, the actuator 520 (or a separate member coupled to the actuator) may extend through a catheter so that a user can manually adjust the position of the actuator, and can selectively move the flexible braid member 514 between the locked and unlocked configurations, from a location outside the patient's body.

In use, the second end 516 of the flexible braid member 514 may be fixed with respect to the body portion 508, while the first end 518 of the flexible braid member may move with the actuator 520. Moving the actuator 520 in the first direction (arrow "A") causes the flexible braid member 514 to assume the unlocked configuration of FIG. 5A in which a first outer diameter "OD1" of the flexible braid member does not hinder movement of the artificial chordae tendineae 502 in the first direction (arrow "A"). Moving the actuator 520 in the second direction (arrow "B") causes the flexible braid member 514 to assume the locked configuration in which the flexible braid member 514 is expanded to have a second outer diameter "OD2" that is larger than the first outer diameter "OD1".

In some embodiments the actuator 520 is movable in the first direction (arrow "A") so that the flexible braid member 514 assumes a second outer diameter "OD2" that is the same as an inner diameter "ID" of the housing portion 512. In this locked configuration, shown in FIG. 5B, the outer diameter "OD2" of the flexible braid member 514 is large enough to press the artificial chordae tendineae 502 into engagement with the sidewall 522 of the housing portion 512. In some embodiments, the force of the flexible braid member 514 against the artificial chordae tendineae 502 results in friction between the artificial chordae tendineae 502, the flexible braid member 514 and the sidewall 522 of the housing portion 512 that prevents the artificial chordae tendineae 502 from moving in either the first or the second direction.

In some embodiments, moving the artificial chordae tendineae in the direction of arrow "A" will tend to tighten the artificial chordae tendineae 502 between the device 500 and the leaflet 150 (FIG. 2) of the heart valve. Where the device 500 is coupled to a papillary muscle or heart wall 152 (FIG. 2), a tension may be achieved in the artificial chordae tendineae 502 to achieve an effect on regurgitation of blood through the heart valve. Observation of regurgitation may be observed via transesophageal echocardiogram, fluoroscopy, or the like to determine whether a target affect has been achieved with the artificial chordae tendineae 502 in place. If, upon observation, the user determines the tension in the artificial chordae tendineae 502 is to be increased, the user may move the actuator 520 in the first direction (arrow "A") to release the artificial chordae tendineae 502 from the frictional lock against the sidewall 522. The user may then apply additional tension to the artificial chordae tendineae (using, for example, a control filament manipulatable from a proximal end of a catheter) to move it further in the first direction (arrow "A"). When a target tension is achieved, the actuator 520 may be moved in the second direction (arrow "B") to lock the artificial chordae tendineae 502 against the sidewall 522. This can be followed by additional observation of regurgitation, followed by additional tensioning, and so on.

If, upon observation, the user determines the tension in the artificial chordae tendineae 502 is to be decreased, the artificial chordae tendineae may be moved in the second direction (arrow "B"). In such a case, the user may move the actuator 520 in the first direction (arrow "A") to release the artificial chordae tendineae 502 from the frictional lock against the sidewall 522, and may reduce tension in the artificial chordae tendineae to move it further in the first direction (arrow "A"). When a reduced tension is achieved, the actuator 520 may be moved in the second direction (arrow "B") to lock the artificial chordae tendineae 502 against the sidewall 522. This can be followed by additional observation of regurgitation, followed by additional tensioning/un-tensioning, and so on.

Upon completion of the tensioning procedure, the actuator 520 may be locked to the housing portion by, for example, crimping, cutting and bonding, swaging or other mechanical technique. The remaining portion of the actuator 520 (i.e., the portion residing in the catheter) may be disconnected from the portion of the actuator remaining locked to the housing portion 512 and may be removed via the catheter. The control filament can similarly be decoupled from the first end 524 of the artificial chordae tendineae 502 and removed via the catheter.

Figure 6A:
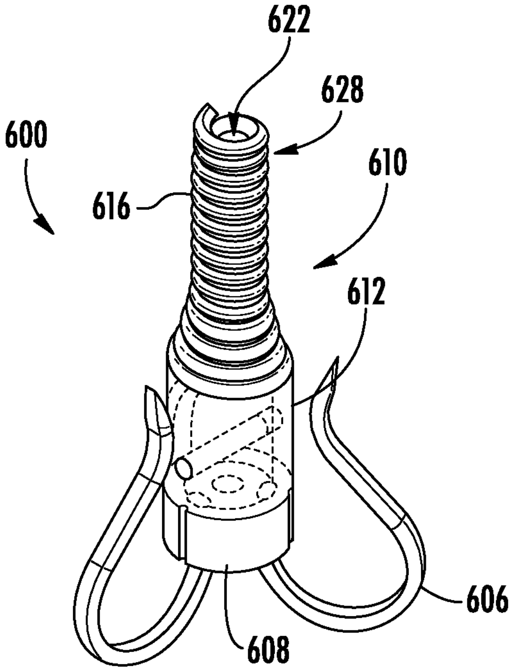
FIGS. 6A, 6B and 6C are perspective, partially transparent perspective, and cross-section views, respectively, of an artificial chordae tendineae tensioning device according to an embodiment of the present disclosure.
Figure 6B:
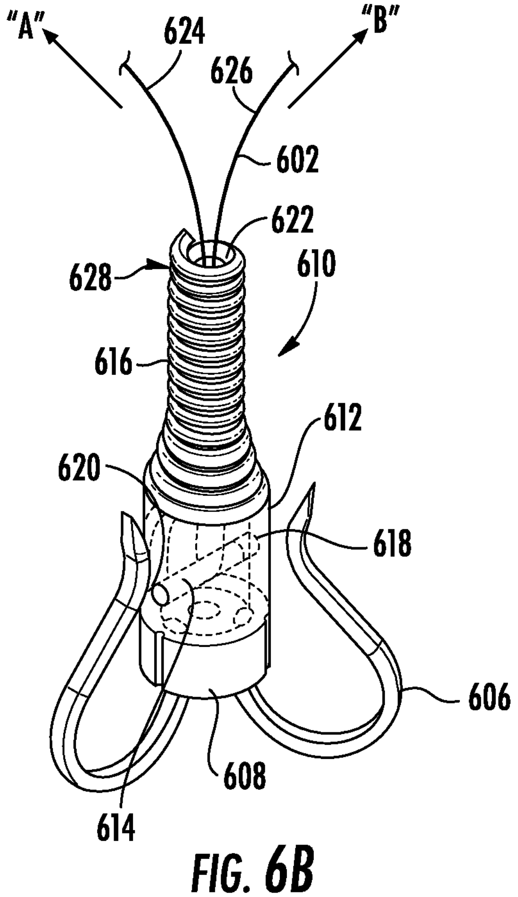
Figure 6C:
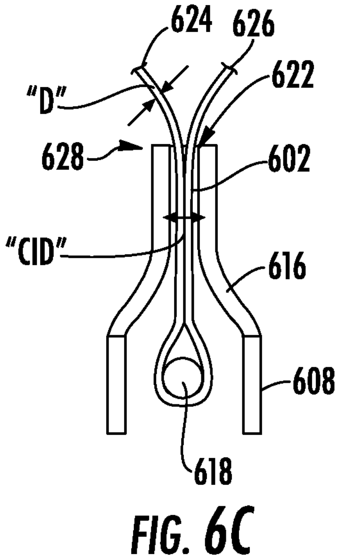
Figure 6D:
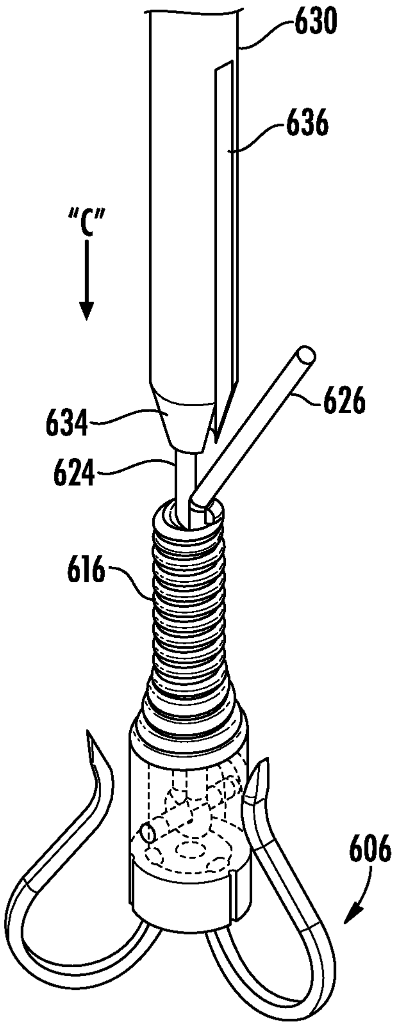
FIGS. 6D-6G are perspective and partially transparent perspective views of the artificial chordae tendineae tensioning device of FIGS. 6A-6C engaged with an embodiment of an actuator.
Figure 6E:
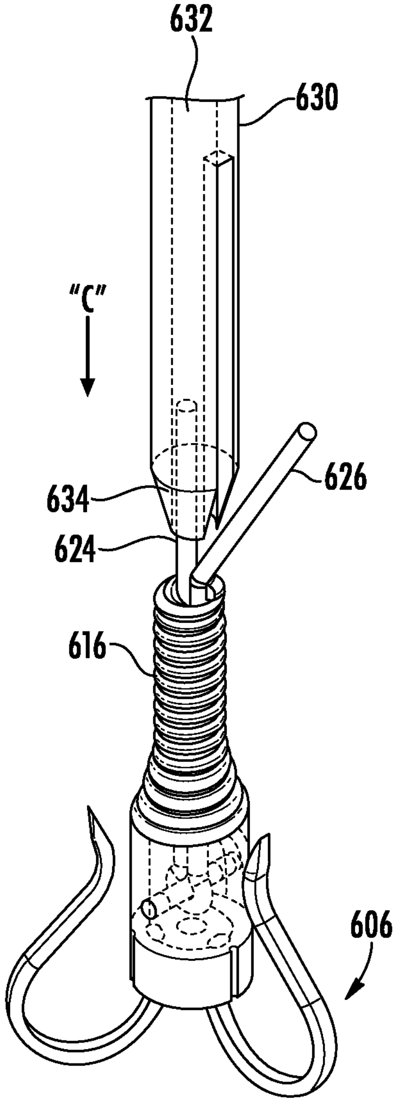

With reference now to FIGS. 6A-6C, an embodiment of a device 600 for adjusting the tension of an artificial chordae tendineae 602 according to the present disclosure is illustrated. The device 600 may comprise an anchor having a tissue-engaging portion 606, a body portion 608 and a locking portion 610. As will be described, the locking portion 610 may be couplable to the artificial chordae tendineae 602 to allow the artificial chordae tendineae to move when the locking portion is in an unlocked configuration and to prevent the artificial chordae tendineae from moving when the locking portion is in a locked configuration. In this manner a user can move the artificial chordae tendineae 602 in a direction tending to increase tension thereon, and when the movement is stopped the artificial chordae tendineae can be held in place by the locking portion 610 to maintain the applied tension.

The artificial chordae tendineae 602 is shown in FIGS. 6A, 6B as having a first end 624 and a second end 626. The first end 624 may, in some embodiments, be coupled to a control filament (not shown) that runs through the catheter to a location in which a user can manipulate the position of (e.g., move) the artificial chordae tendineae 602. In some embodiments the first end 624 may include a loop or other connection mechanism (not shown) through which the control filament may be coupled. Upon completion of the tensioning procedure, the control filament may be detached from the first end 624 and removed via the catheter. The second end 626 of the artificial chordae tendineae 602 may extend within the heart to couple directly or indirectly to one or more leaflet clips 206 (FIG. 2). In some embodiments the second end 626 may couple to a filament 200 (FIG. 2) that, in turn, couples to one or more leaflet clips 206.

In the illustrated embodiment the locking portion 610 comprises a housing portion 612 within which a bearing member 614 is disposed, and a coil portion 616 coupled to an end of the housing portion 612 opposite the body portion 608. The bearing member 614 may be disposed within the housing portion 612 such that it is oriented perpendicular to the artificial chordae tendineae 602. The bearing member 614 may be coupled at opposite ends to opposing inner surfaces 618, 620 of the housing portion 612 to lock the bearing member to the housing portion. In some non-limiting example embodiments, the bearing member 614 may be rotatable about its axis with respect to the housing portion 612. The artificial chordae tendineae 602 may be disposed through a longitudinal opening 622 in the coil portion 616 and may loop around the bearing member 614 so that first and second ends 624, 626 of the artificial chordae tendineae extend through an upper end 628 of the coil portion.

As can best be seen in FIG. 6C, the longitudinal opening 622 in the coil portion 616 may have an inner diameter "CID" that is smaller than twice the diameter "D" of the artificial chordae tendineae 602 when the locking portion 610 is in the locked configuration. Thus, in the locked configuration the coil portion 616 may apply an inward force to the two portions of artificial chordae tendineae 602 to squeeze them together to prevent the artificial chordae tendineae from moving with respect to the coil portion.

To arrange the locking portion 610 in the unlocked configuration, an actuator 630 may engage the coil portion 616 to selectively increase the inner diameter "CID" to reduce the force applied to the two portions of artificial chordae tendineae 602 by an amount to allow the artificial chordae tendineae to move through the coil portion 616. In some embodiments, the actuator 630 (or a separate member coupled to the actuator) may extend through a catheter so that a user can manually adjust the position of the actuator from a location outside the patient's body.

The actuator 630 may be a hollow push rod having a lumen 632 and a tapered tip portion 634. The lumen 632 may be sized so that its inner diameter is greater than twice the diameter "D" of the artificial chordae tendineae 602 to enable the artificial chordae tendineae to move freely within. The actuator 630 may also include a longitudinal slot 636 to allow the second end 626 of the artificial chordate tendineae to protrude therefrom to lead to the leaflet clip 206 (FIG. 2). The first end 624 can be received within the lumen 632 of the actuator 630 to connect to the control filament in a manner previously described.

Figure 6F:
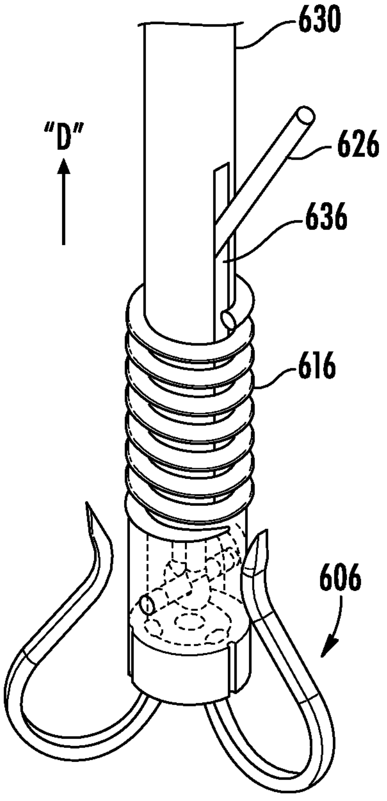
Figure 6G:
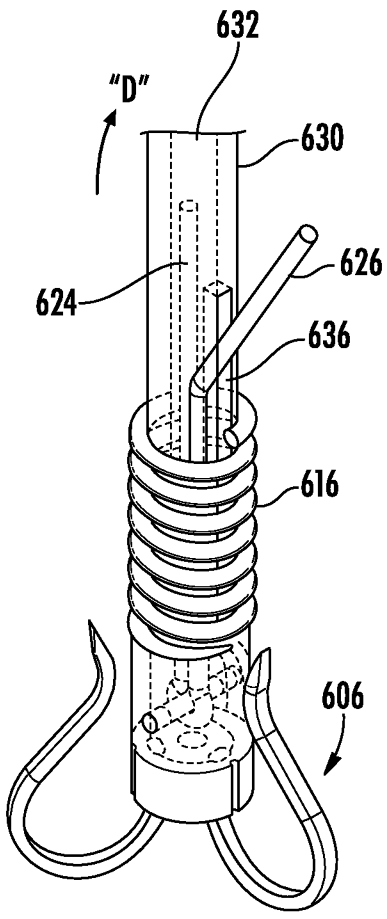

In use, moving the actuator 630 in a first direction "C" causes the tapered tip portion 634 to engage the upper end 628 of the coil portion 616. Driving the actuator 630 further in the first direction "C" spreads the coil portion 616 apart, increasing the inner diameter "CID" of the coil portion 616. In use, the actuator 630 may be driven into engagement with the coil portion 616 until the tapered tip portion 634 is positioned adjacent to the bearing member 614. In this position, shown in FIGS. 6F and 6G, the coil portion 616 is in an expanded configuration such that it does not pinch the artificial chordae tendineae. The locking portion 610 is thus shown in the unlocked configuration which allows the user to adjust the position of the artificial chordae tendineae to adjust tension between the device 600 and one or more attached leaflet clips 206 (FIG. 2). Moving the actuator 630 in a second direction "D" allows the inner diameter "CID" of the coil portion 616 to return the locking portion 610 to the locked configuration in which the inner diameter "CID" of the coil portion is smaller than twice the diameter "D" of the artificial chordae tendineae 602, thus preventing the artificial chordae tendineae from moving in the first or second directions "A", "B".

In some embodiments, movement of the artificial chordae tendineae 602 in the direction of arrow "A" will tend to tighten the artificial chordae tendineae 602 between the device 600 and the leaflet 150 (FIG. 2) of the heart valve. Where the device 600 is coupled to a papillary muscle or heart wall 152 (FIG. 2), a target tension may be achieved in the artificial chordae tendineae 602 to achieve a target effect on regurgitation of blood through the heart valve. Observation of regurgitation may be observed via transesophageal echocardiogram, fluoroscopy, or the like to determine whether a target affect has been achieved with the artificial chordae tendineae 602 in place. If, upon observation, the user determines the tension in the artificial chordae tendineae 602 is to be increased, the user may move the actuator 630 to expand the inner diameter "CID" of the coil portion 616 to release the segments of artificial chordae tendineae 602 from the frictional lock against each other and the inner surfaces of the coil portion, so that the user may apply additional tension to the artificial chordae tendineae to move it further in the first direction (arrow "A"). When a target tension is achieved, the actuator 630 may be moved to return the inner diameter "CID" of the coil portion 616 to its original position, locking the segments of artificial chordae tendineae 602 to each other and to the inner surfaces of the coil portion. This can be followed by additional observation of regurgitation, followed by additional tensioning, and so on.

If, upon observation, the user determines the tension in the artificial chordae tendineae 602 is to be decreased, the artificial chordae tendineae may be moved in the second direction (arrow "B"). In such a case, the user may move the actuator 630 to release the segments of artificial chordae tendineae 602 from the frictional lock against each other and the inner surfaces of the coil portion 616, so that the user may reduce tension in the artificial chordae tendineae to move it in the second direction (arrow "B"). When a target reduced tension is achieved, the actuator 630 may be moved to return the inner diameter "CID" of the coil portion 616 to its original position, locking the segments of artificial chordae tendineae 602 to each other and to the inner surfaces of the coil portion. This can be followed by additional observation of regurgitation, followed by additional tensioning/de-tensioning, and so on.

Upon completion of the tensioning procedure, the actuator 630 may be locked to the housing portion by, for example, crimping, cutting and bonding, swaging or other mechanical technique. The remaining portion of the actuator 630 (i.e., the portion residing in the catheter) may be disconnected and may be removed via the catheter.

Figure 7A:
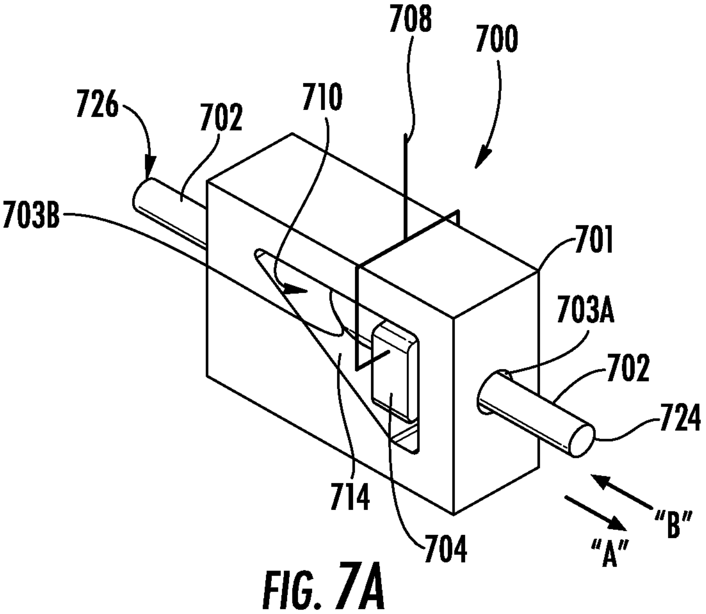
FIGS. 7A and 7B are perspective and cross-section views, respectively, of a locking portion according to an embodiment of the present disclosure.
Figure 7B:
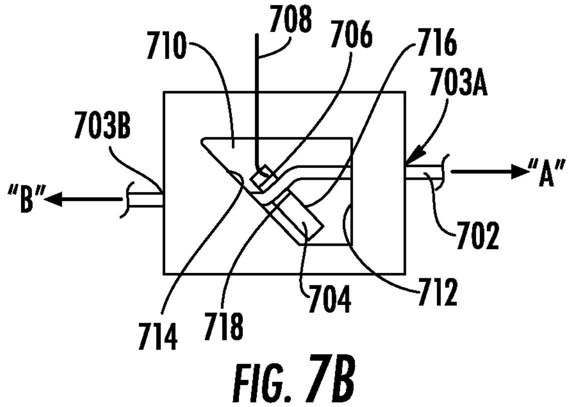

Referring now to FIGS. 7A-7B, an embodiment of a locking portion 700 for adjusting the tension of an artificial chordae tendineae 702 according to the present disclosure is illustrated. The locking portion 700 may be interchanged, as appropriate, with any of the locking portions disclosed in relation to the devices 300-600 of FIGS. 3A-6A. Thus, the locking portion 700 may be combined with any of the a tissue-engaging portions, body portions and housing portions previously described in order to provide an anchor that includes features that enable a user to tension and/or de-tension as well as lock an artificial chordae tendineae between the anchor, which may be coupled to a papillary muscle or heart wall, and a clip, which may be coupled to a leaflet of a heart valve.

As will be described, the locking portion 700 may be couplable to the artificial chordae tendineae 702 to allow the artificial chordae tendineae to move in a first direction (arrow "A") while preventing the artificial chordae tendineae from moving in a second direction (arrow "B") opposite the first direction. In this manner a user can move the artificial chordae tendineae 702 in a direction tending to increase tension thereon, and when the movement is stopped the artificial chordae tendineae will be held in place by the locking portion 700 to thereby maintain the applied tension.

The artificial chordae tendineae is shown in FIGS. 7A, 7B as having a first end 724 and a second end 726. The first end 724 may, in some embodiments, be coupled to a control filament (not shown) that runs through the catheter to a location in which a user can manipulate the position of (e.g., move) the artificial chordae tendineae 702. In some embodiments the first end 724 may include a loop or other connection mechanism through which the control filament may be coupled. Upon completion of the tensioning procedure, the control filament may be detached from the first end 724 and removed via the catheter. The second end 726 of the artificial chordae tendineae 702 may extend within the heart to couple directly or indirectly to one or more leaflet clips 206 (FIG. 2). In some embodiments the second end 726 may couple to a filament 200 (FIG. 2) that, in turn, couples to one or more leaflet clips 206.

In the illustrated embodiment the locking portion 700 comprises a body portion 701 with openings 703A, B through which the artificial chordae tendineae 702 is disposed. The body portion 701 may house a locking body 704 having a bore 706 for receiving the artificial chordae tendineae 702 therethrough. The locking body 704 may be a generally rectangular member (though the specific shape is not critical), coupled to an actuator 708 that can be used to move the locking body within the body portion 701.

The locking body 704 can be received within an opening 710 in the body portion 701. The opening 710 may have first and second walls 712, 714. In the illustrated embodiment, the first wall 712 is oriented parallel to a first side 716 of the locking body 704 when the locking portion 700 is in the unlocked configuration (FIG. 7A). The second wall 714 may be oriented at an oblique angle with respect to the first wall 712.

In the unlocked configuration of FIG. 7A, the artificial chordae tendineae 702 is disposed along a substantially linear path through the openings 703A, B in the body portion 701 and the bore 706 of the locking body 704. In this configuration, the artificial chordae tendineae 702 is movable in the first and second directions (arrows "A" and "B", respectively) to increase or decrease tension in the artificial chordae tendineae.

To lock the artificial chordae tendineae 702 in place, the actuator 708 may be moved in the first direction (arrow "A"). This movement may cause the locking body 704 to move in the first direction (arrow "A") until the locking body engages the angled second wall 714 of the opening 710 in the body portion 701. Upon engagement with the angled second wall 714, a lower portion of the locking body 704 may stop moving, while an upper portion of the locking body may continue to move until it approaches the angled second wall, which results in the locking body rotating to assume the tilted configuration shown in FIG. 7B. In this configuration (referred to as the locked configuration), the bore 706 in the locking body 704 is oriented at an oblique angle with respect to the first and second openings 703A, B in the body portion 701. In this orientation the locking body 704 pinches the artificial chordae tendineae 702 so that it is no longer free to move through the bore 706 or the first and second openings 703A, B.

Thus arranged, by moving the actuator 708 in the first and second directions (arrows "A" and "B"), a user can selectively lock and unlock the locking portion 700. In some embodiments, the actuator 708 (or a separate member coupled to the actuator) may extend through a catheter so that a user can manually adjust the position of the actuator from a location outside the patient's body.

The locking portion 700 may also be locked and unlocked without an actuator. Thus, in some embodiments, when the artificial chordae tendineae 702 is moved in the first direction "A", frictional forces between the artificial chordae tendineae and the locking body 704 may cause the locking body to move toward the first wall 712, aligning the bore 706 with the openings 703A, B in the body portion 701, and unlocking the locking portion 700. Likewise, when the artificial chordae tendineae 702 is moved in the second direction "B", frictional forces between the artificial chordae tendineae and the locking body 704 can cause the locking body 704 to move toward the second wall 714, causing the locking body to tilt (FIG. 7B), and pinching the artificial chordae tendineae within the bore 706 and preventing the artificial chordae tendineae from further movement therethrough.

Tensioning and de-tensioning of the artificial chordae tendineae 702 may be achieved by unlocking the locking portion 700, adjusting the tension, then re-locking the locking portion. Visualization, followed by re-adjustment of tension in the artificial chordae tendineae 702 may be performed in the manner previously described in relation to the embodiments of FIGS. 1-6C.

Upon completion of the tensioning procedure, the actuator 708 may be locked in place by, for example, crimping, cutting and bonding, swaging or other mechanical technique. The remaining portion of the actuator 708 (i.e., the portion residing in the catheter) may be disconnected from the portion of the actuator and may be removed via the catheter.

Figure 8A:
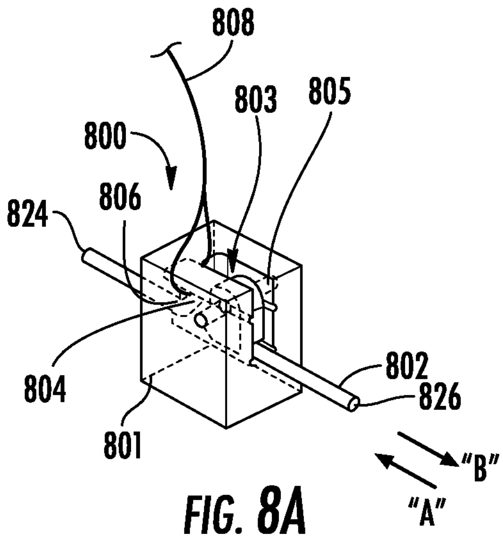
FIGS. 8A-8E are transparent views of locking portions according to embodiments of the present disclosure.

Referring now to FIG. 8A, an embodiment of a locking portion 800 for adjusting the tension of an artificial chordae tendineae 802 according to the present disclosure is illustrated. The locking portion 800 may be interchanged, as appropriate, with any of the locking portions disclosed in relation to the devices 300-600 of FIGS. 3A-6A. Thus, the locking portion 800 may be combined with any of the a tissue-engaging portions, body portions and housing portions previously described in order to provide an anchor that includes features that enable a user to tension and/or de-tension as well as lock an artificial chordae tendineae between the anchor, which may be coupled to a papillary muscle or heart wall, and a clip, which may be coupled to a leaflet of a heart valve.

As will be described, the locking portion 800 may be couplable to the artificial chordae tendineae 802 to allow the artificial chordae tendineae to move in a first direction (arrow "A") while preventing the artificial chordae tendineae from moving in a second direction (arrow "B") opposite the first direction. In this manner a user can move the artificial chordae tendineae 802 in a direction tending to increase tension thereon, and when the movement is stopped the artificial chordae tendineae will be held in place by the locking portion 800 to thereby maintain the applied tension.

The artificial chordae tendineae is shown in FIG. 8A as having a first end 824 and a second end 826. The first end 824 may, in some embodiments, be coupled to a control filament (not shown) that runs through the catheter to a location in which a user can manipulate the position of (e.g., move) the artificial chordae tendineae 802. In some embodiments the first end 824 may include a loop or other connection mechanism through which the control filament may be coupled. Upon completion of the tensioning procedure, the control filament may be detached from the first end 824 and removed via the catheter. The second end 826 of the artificial chordae tendineae 802 may extend within the heart to couple directly or indirectly to one or more leaflet clips 206 (FIG. 2). In some embodiments the second end 826 may couple to a filament 200 (FIG. 2) that, in turn, couples to one or more leaflet clips 206.

In the illustrated embodiment the locking portion 800 comprises a body portion 801 having an opening 803 through which the artificial chordae tendineae 802 is disposed. The body portion 801 may house a rotatable locking body 804 having an engagement surface 806 for selectively engaging the artificial chordae tendineae 802. In some embodiments the engagement surface 806 may have a curved shape and can also include surface texturing or surface features configured to enhance engagement between the engagement surface and the artificial chordae tendineae. The rotatable locking body 804 may further be coupled to a pin 805, which in turn is coupled to the body portion 801, thus allowing the rotatable locking body to rotate with respect to the body portion 801.

Thus arranged, when the artificial chordae tendineae 802 is moved in the first direction (arrow "A"), contact between the artificial chordae tendineae and the engagement surface 806 of the rotatable locking body 804 causes the rotatable locking body to rotate about the pin 805 so that the rotatable locking body does not pinch the artificial chordae tendineae. When the artificial chordae tendineae 802 is moved in the second direction (arrow "B"), contact between the artificial chordae tendineae and the engagement surface 806 of the rotatable locking body 804 causes the rotatable locking body to rotate about the pin 805 in the reverse direction, causing the rotatable locking body to pinch the artificial chordae tendineae between the engagement surface and the body portion 801, preventing further movement of the artificial chordae tendineae.

In some embodiments, movement of the artificial chordae tendineae 802 in the direction of arrow "A" will tend to increase tension between the artificial chordae tendineae and the leaflet 150 (FIG. 2) of the heart valve. Where the locking portion 800 is incorporated into a device is coupled to a papillary muscle or heart wall 152, a target tension may be achieved in the artificial chordae tendineae 802 to achieve a target effect on regurgitation of blood through the heart valve. Observation of regurgitation may be observed via transesophageal echocardiogram, fluoroscopy, or the like to determine whether a target affect has been achieved with the artificial chordae tendineae 802 in place. If, upon observation, the user determines the tension in the artificial chordae tendineae 802 is to be increased, the user may apply additional tension to the artificial chordae tendineae to move it further in the first direction (arrow "A"), followed by additional observation, and so on.

If, upon observation, the user determines the tension in the artificial chordae tendineae 802 is to be decreased, the artificial chordae tendineae may be moved in the second direction (arrow "B"). As described, however, the arrangement of the locking portion 800 may prevent movement of the artificial chordae tendineae 802 in the second direction. Thus, the locking portion 800 may include an actuator 808 configured to manually rotate the rotatable locking body 804 away from the artificial chordae tendineae to reduce the frictional forces between the artificial chordae tendineae 802, the rotatable locking body and the body portion 801 so that the artificial chordae tendineae 802 can move in the second direction (arrow "B"), which can result in a target reduction in tension in the artificial chordae tendineae. In the illustrated embodiment the actuator 808 is a filament disposed through a central portion of the rotatable locking body 804. The actuator 808 may run through the catheter to a location in which a user can actuate the actuator to "unlock" the locking portion 800.

Once tension has been reduced, observation of regurgitation may be observed via transesophageal echocardiogram, fluoroscopy, or the like to determine whether a target affect has been achieved. Additional adjustments of the artificial chordae tendineae 802 in the first and/or second directions can be made until a target effect on heart valve regurgitation is achieved. Upon completion of the tensioning procedure, the actuator 808 may be detached from the rotatable locking body 804 and removed via the catheter.

Figure 8B:
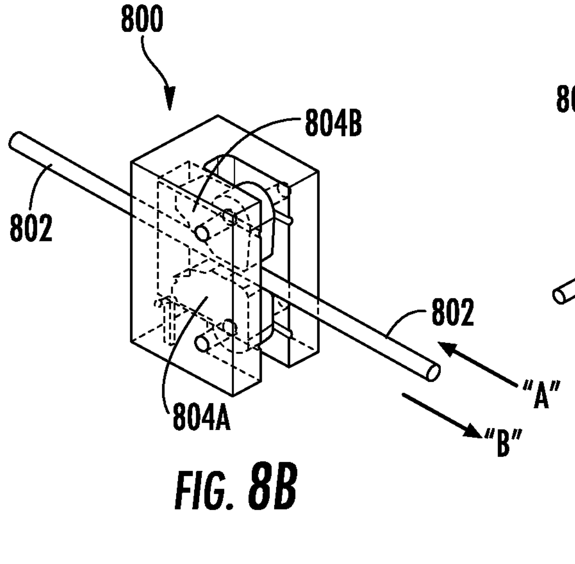

FIG. 8B illustrates an alternative embodiment of a locking portion 800 including first and second opposing rotatable locking bodies 804A, B, which may accept the artificial chordae tendineae 802 therebetween. The operation of this embodiment may be the same or similar to that of the embodiment of FIG. 8A. For example, as the artificial chordae tendineae tries to move in direction "B" it will rotate both locking bodies 804A, B which will pinch the artificial chordae tendineae therebetween.

Figure 8C:
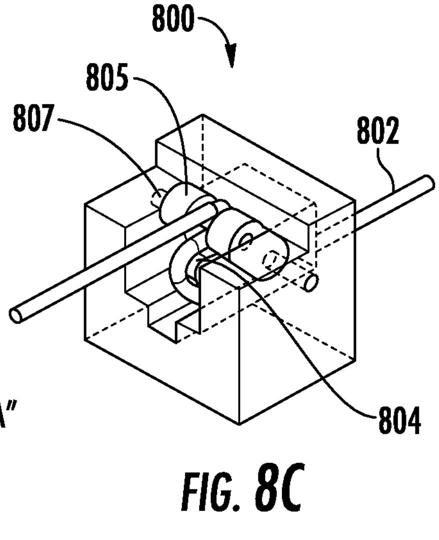
Figure 8D:
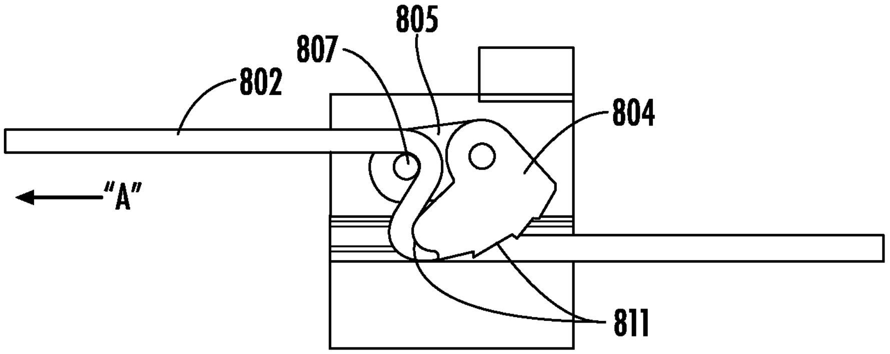
Figure 8E:
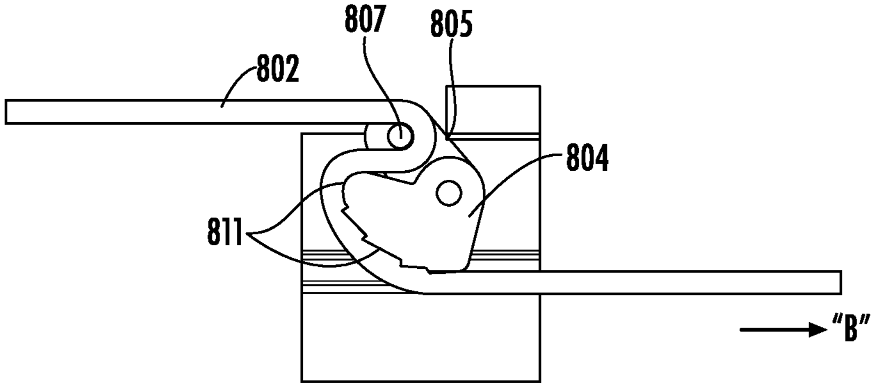

FIGS. 8C-8D illustrate a further alternative embodiment of a locking portion 800 including a single rotatable locking body 804 and an alignment member 809. The alignment member 805 may be fixed to the rotatable locking body 804 to maintain the rotatable locking body in a target orientation during operation. The alignment member 809 may include a bearing member 807 around which the artificial chordae tendineae 802 is disposed, forcing the artificial chordae tendineae 802 to traverse a predetermined serpentine path through the locking portion 800. Thus, when the artificial chordae tendineae 802 is moved in the first direction (arrow "A"), in addition to the force applied to the engagement surfaces 811 of the rotatable locking body 804, the artificial chordae tendineae also applies a force to the bearing member 807 tending to cause the alignment member 809 to pull upward on the locking body 804 to rotate the rotatable locking body from the locked configuration (FIG. 8D) to the unlocked configuration (FIG. 8E). Likewise, when the artificial chordae tendineae 802 is moved in the second direction (arrow "B"), in addition to the force applied to the engagement surfaces 811 of the locking body, the artificial chordae tendineae also applies a force to the bearing member 807 tending to cause the alignment member 809 to pull down on the locking body 804 to rotate the rotatable locking body from the unlocked configuration (FIG. 8E) to the locked configuration (FIG. 8D).

Referring now to FIGS. 9A-9E, various embodiments of a locking portion 900A-E for adjusting the tension of an artificial chordae tendineae 902 according to the present disclosure is illustrated. In some embodiments, the artificial chordae tendineae 902 may have a first end 924 that can be coupled to a control filament (not shown) that runs through the catheter to a location in which a user can manipulate the position of (e.g., move) the artificial chordae tendineae 902. The artificial chordae tendineae may have a second end 926 that may extend within the heart to couple directly or indirectly to one or more leaflet clips 206 (FIG. 2). In some embodiments the second end 926 may couple to a filament 200 (FIG. 2) that, in turn, couples to one or more leaflet clips 206. The locking portions 900A-E may be interchanged, as appropriate, with any of the locking portions disclosed in relation to the devices 300-600 of FIGS. 3A-6A. Thus, the locking portions 900A-E may be combined with any of the a tissue-engaging portions, body portions and housing portions previously described in order to provide an anchor that includes features that enable a user to tension and/or de-tension as well as lock an artificial chordae tendineae between the anchor, which may be coupled to a papillary muscle or heart wall, and a clip, which may be coupled to a leaflet of a heart valve.

Embodiments of the locking portions 900A-E include a variety of common features. For example, each of the locking portions 900A-E can include a body portion 901A-E and a clamping element 904A-E, where the clamping element is biased into engagement with the body portion 901A-E to clamp a portion of an artificial chordae tendineae 902 therebetween. In some non-limiting example embodiments, the clamping element 904A-E may be biased into engagement with the body portion 901A-E via a hinge 905A-E, which in some embodiments is a living hinge comprising a thin flexible hinge made from the same material as the clamping element and the body portion. The clamping element 904A-E can be an integrally formed portion of the body portion 901A-E, or it can be a separate piece that is coupled to the body portion by any appropriate technique (e.g., welding, gluing, press-fit).

The clamping element 904A-E can have a clamping face 906A-E that engages the artificial chordae tendineae 902 and presses the artificial chordae tendineae against an engagement face 910A-E of the corresponding body portion 901A-E. The clamping face 906A-E can have any of a variety of shapes and can also or alternatively include surface texturing or coating, to enhance engagement between the clamping face and the artificial chordae tendineae 902. The engagement face 910A-E may have corresponding or cooperating shapes to those of the associated clamping face 906A-E, and may also include surface texturing or coating, to enhance engagement between the engagement face and the artificial chordae tendineae 902.

Figure 9A:
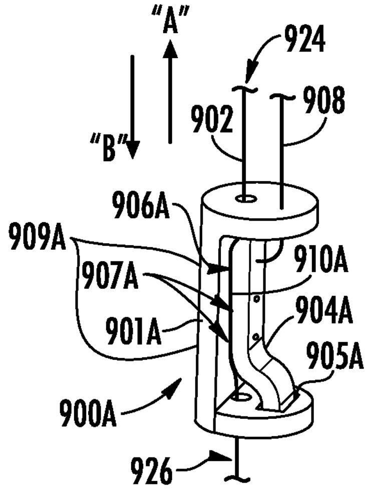
FIGS. 9A-9E are perspective views of clamp-style locking portions according to an embodiment of the present disclosure.
Figure 9B:
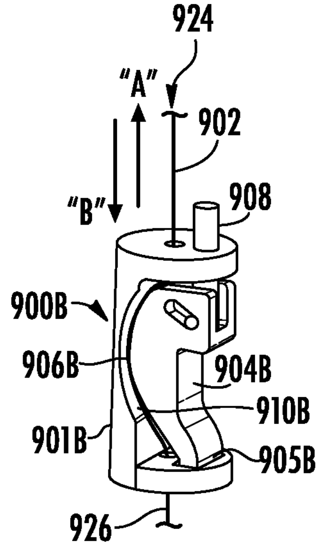
Figure 9C:
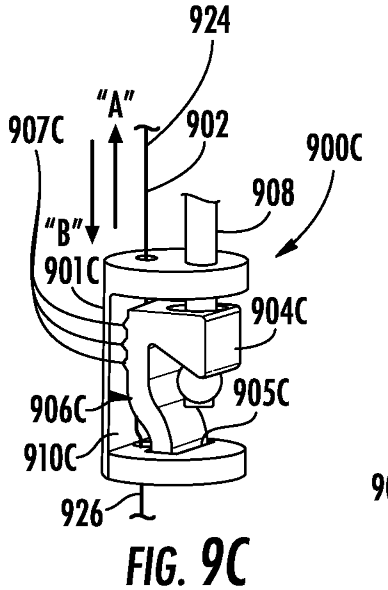
Figure 9D:
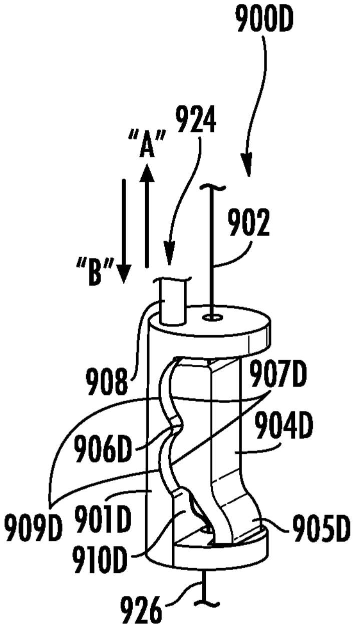
Figure 9E:
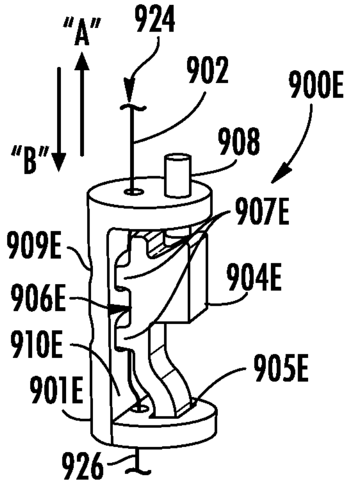

The locking portion 900A of FIG. 9A includes a clamping face 906A having a plurality of barbs 907A that are receivable within corresponding recesses 909A in the engagement face 910A of the body portion 901A. The locking portion 900B of FIG. 9B includes a clamping face 906B having a curved geometry that is receivable by a corresponding curved surface of the engagement face 910B of the body portion 901B. The locking portion 900C of FIG. 9C includes a clamping face 906C having a plurality of barbs 907C that are engageable with a flat surface of the engagement face 910C of the body portion 901C. The locking portion 900D of FIG. 9D includes a clamping face 906D comprising a plurality of curved portion 907D that are receivable within corresponding recesses 909D in the engagement face 910D of the body portion 901D. The locking portion 900E of FIG. 9E includes a clamping face 906E having a plurality of protrusions 907E that are receivable within corresponding recesses 909E in the engagement face 910E of the body portion 901E.

The locking portions 900A-E are illustrated in the locked configuration. Thus, in the illustrated configurations the locking portions 900A-E allow the artificial chordae tendineae 902 to move in a first direction (arrow "A") and prevent the artificial chordae tendineae from moving in a second direction (arrow "B") opposite the first direction. As can be appreciated, moving the artificial chordae tendineae 902 in the first direction (arrow "A") tends to move the clamping element 904A-E away from the associated body portion 901A-E, reducing friction between the components and allowing the artificial chordae tendineae to pass. By contrast, moving the artificial chordae tendineae in the second direction (arrow "B") tends to move the clamping element 904A-E toward the associated body portion 901A-E, which increases friction between the components and locks the artificial chordae tendineae to the locking portion 900A-E.

In some embodiments, moving of the artificial chordae tendineae 902 in the direction of arrow "A" will tend to increase tension between the artificial chordae tendineae and the leaflet 150 (FIG. 2) of the heart valve. Where the locking portion 900A-E is incorporated into a device that is coupled to a papillary muscle or heart wall 152, a target tension may be achieved in the artificial chordae tendineae 902 to achieve a target effect on regurgitation of blood through the heart valve. Observation of regurgitation may be observed via transesophageal echocardiogram, fluoroscopy, or the like to determine whether a target affect has been achieved with the artificial chordae tendineae 902 in place. If, upon observation, the user determines the tension in the artificial chordae tendineae 902 is to be increased, the user may apply additional tension to the artificial chordae tendineae to move it further in the first direction (arrow "A"), followed by additional observation, and so on.

If, upon observation, the user determines the tension in the artificial chordae tendineae 902 is to be decreased, the artificial chordae tendineae may be moved in the second direction (arrow "B"). As described, however, the arrangement of the locking portion 900A-E may prevent movement of the artificial chordae tendineae 902 in the second direction. Thus, the locking portion 900A-E may include an actuator 908 configured to manually rotate the clamping element 904A-E about the hinge 905A-E to move the clamping element away from the artificial chordae tendineae and the body portion 901A-E to reduce the frictional forces between the artificial chordae tendineae 902, the clamping element 904A-E and the body portion 901A-E to allow the artificial chordae tendineae 902 to move in the second direction (arrow "B"). Moving the artificial chordae tendineae 902 in the second direction can result in a target reduction in tension in the artificial chordae tendineae. In the illustrated embodiment the actuator 908 is a filament coupled to the clamping element 904A-E of the locking portion 900A-E. The actuator 908 may run through the catheter to a location in which a user can actuate the actuator to "unlock" the locking portion 900A-E.

Once tension has been reduced, observation of regurgitation may be observed via transesophageal echocardiogram, fluoroscopy, or the like to determine whether a target affect has been achieved. Additional adjustments of the artificial chordae tendineae 902 in the first and/or second directions can be made until a target effect on heart valve regurgitation is achieved. Upon completion of the tensioning procedure, the actuator 908 may be detached from the locking portion 900A-E and may be removed via the catheter.

Figure 10A:
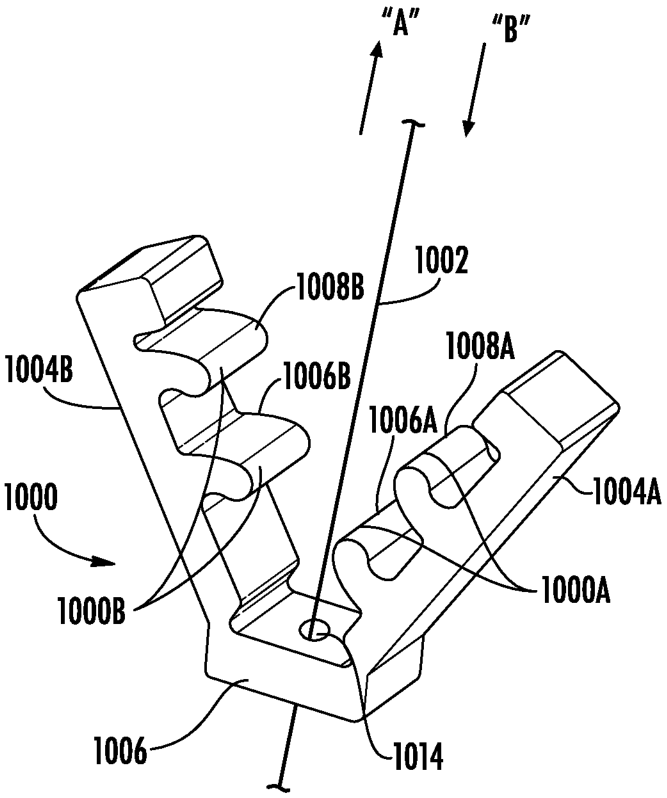
FIGS. 10A and 10B are perspective views of a clamp-style locking portion according to an embodiment of the present disclosure.
Figure 10B:
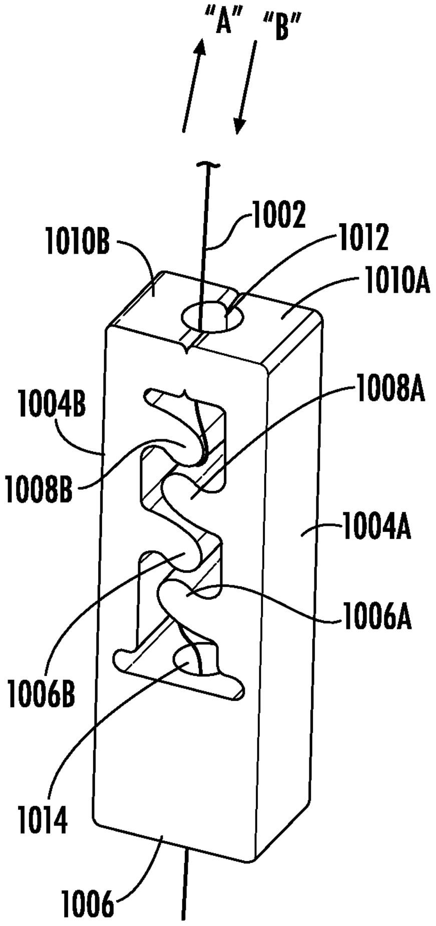
Figure 10C:
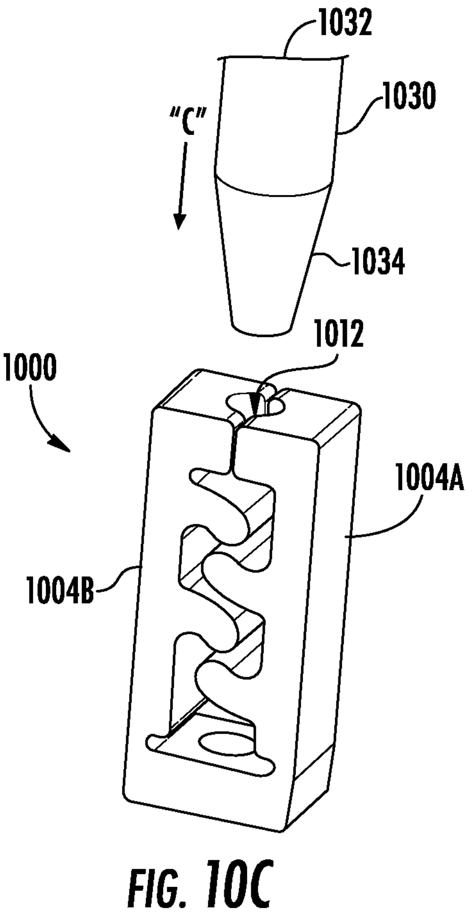
FIGS. 10C and 10D are perspective views of the artificial chordae tendineae tensioning device of FIGS. 10A and 10B engaged with an embodiment of an actuator.

Referring now to FIGS. 10A and 10B, an embodiment of a locking portion 1000 for adjusting the tension of an artificial chordae tendineae 1002 according to the present disclosure is illustrated. The locking portion 1000 may be interchanged, as appropriate, with any of the locking portions disclosed in relation to the devices 300-600 of FIGS. 3A-6A. Thus, the locking portion 1000 may be combined with any of the a tissue-engaging portions, body portions, and housing portions previously described in order to provide an anchor that includes features that enable a user to tension and/or de-tension as well as lock an artificial chordae tendineae between the anchor, which may be coupled to a papillary muscle or heart wall, and a clip, which may be coupled to a leaflet of a heart valve.

The locking portion 1000 may comprise first and second clamp members 1004A, B coupled at one end by a hinge 1006, which in one non-limiting example embodiment is a living hinge. The first and second clamp members 1004A, B may be biased toward each other (e.g., in the closed configuration shown in FIG. 10B) by the living hinge. The first and second clamp member 1004A, B can each have a clamping face 1000A, B for engaging an artificial chordae tendineae 1002 therebetween. In the illustrated embodiment the clamping faces 1000A, B include a plurality of protrusions 1006A, B; 1008A, B. Each of the plurality of projections can be received between adjacent projections of the opposing clamping face 1000A, B.

An upper end 1010A, B of each of the first and second clamp members 1004A, B may combine to form an opening 1012 for receiving the artificial chordae tendineae 1002 therethrough. An opening 1014 can also be provided in the hinge 1006 for receiving the artificial chordae tendineae 1002 therethrough.

FIG. 10A shows the locking portion 1000 illustrated in the unlocked configuration, which may allow the artificial chordae tendineae 1002 to move with respect to the locking portion. By contrast, FIG. 10B shows the locking portion 1000 in the locked configuration, in which the artificial chordae tendineae 1002 is prevented from moving with respect to the locking portion. As will be understood, in the locked configuration the artificial chordae tendineae 1002 is forced to conform to the shape of the plurality of protrusions 1006A, B; 1008A, B. Frictional forces between the protrusions and the artificial chordae tendineae 1002 may prevent the artificial chordae tendineae from moving in either the first or second direction.

In some embodiments, moving of the artificial chordae tendineae 1002 in the direction of arrow "A" will tend to increase tension between the artificial chordae tendineae and the leaflet 150 (FIG. 2) of the heart valve. In such a case, the user may reconfigure the locking portion 1000 to assume the unlocked configuration (FIG. 10B) to allow the artificial chordae tendineae 1002 to move in the first direction (arrow "A") to increase tension in the artificial chordae tendineae. Where the locking portion 1000 is incorporated into a device that is coupled to a papillary muscle or heart wall 152, a target tension may be achieved in the artificial chordae tendineae 1002 to achieve a target effect on regurgitation of blood through the heart valve. Observation of regurgitation may be observed via transesophageal echocardiogram, fluoroscopy, or the like to determine whether a target affect has been achieved with the artificial chordae tendineae 1002 in place. If, upon observation, the user determines the tension in the artificial chordae tendineae 1002 is to be increased, the locking portion may be unlocked, and the user may apply additional tension to the artificial chordae tendineae to move it further in the first direction (arrow "A"), followed by additional observation, and so on.

If, upon observation, the user determines the tension in the artificial chordae tendineae 1002 is to be decreased, the artificial chordae tendineae may be moved in the second direction (arrow "B"). In such a case, the user may reconfigure the locking portion 1000 to assume the unlocked configuration (FIG. 10B) to allow the artificial chordae tendineae 1002 to move in the second direction (arrow "B") to reduce tension in the artificial chordae tendineae. When a target reduced tension is achieved, the locking portion 1000 may be reconfigured to assume the locked configuration (FIG. 10A) to lock the artificial chordae tendineae 1002 to the locking portion 1000. This can be followed by additional observation of regurgitation, followed by additional tensioning/un-tensioning, and so on.

To arrange the locking portion 1000 in the unlocked configuration, an actuator 1030 may engage the first and second clamp member 1004A, B to move them apart, thus reducing or eliminating the clamping force applied to the artificial chordae tendineae (not shown) so that the artificial chordae tendineae 1002 can move through the locking portion. In some embodiments, the actuator 1030 (or a separate member coupled to the actuator) may extend through a catheter so that a user can manually adjust the position of the actuator from a location outside the patient's body.

The actuator 1030 may be a hollow push rod having a lumen 1032 and a tapered tip portion 1034. The lumen 1032 may be sized to accommodate the artificial chordae tendineae 1002 and to enable the artificial chordae tendineae to move freely within.

Figure 10D:
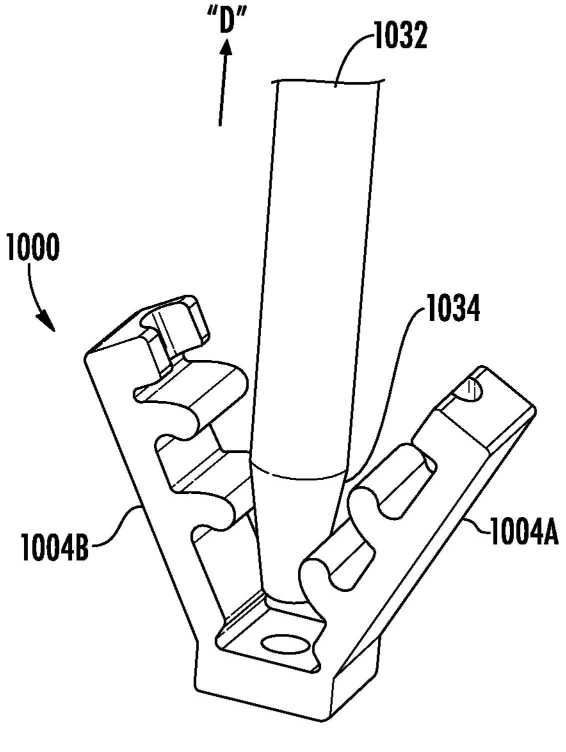

In use, moving the actuator 1030 in a first direction "C" causes the tapered tip portion 1034 to engage the opening 1012 formed by the first and second clamp members 1004A, B. Driving the actuator 1030 further in the first direction "C" spreads the first and second clamp members 1004A, B apart by an amount so that the artificial chordae tendineae 1002 can move in the first and second direction (arrows "A", "B" in FIGS. 10A, B). The user may then adjust the position of the artificial chordae tendineae 1002 to adjust tension between the anchor and one or more attached leaflet clips 206 (FIG. 2). Moving the actuator 1030 in a second direction "D" (FIG. 10D) allows the first and second clamp members 1004A, B to return the locking portion 1000 to the locked configuration in which the first and second clamp members clamp against the artificial chordae tendineae 1002, thus preventing the artificial chordae tendineae from moving in the first or second directions "A", "B".

Figure 11A:
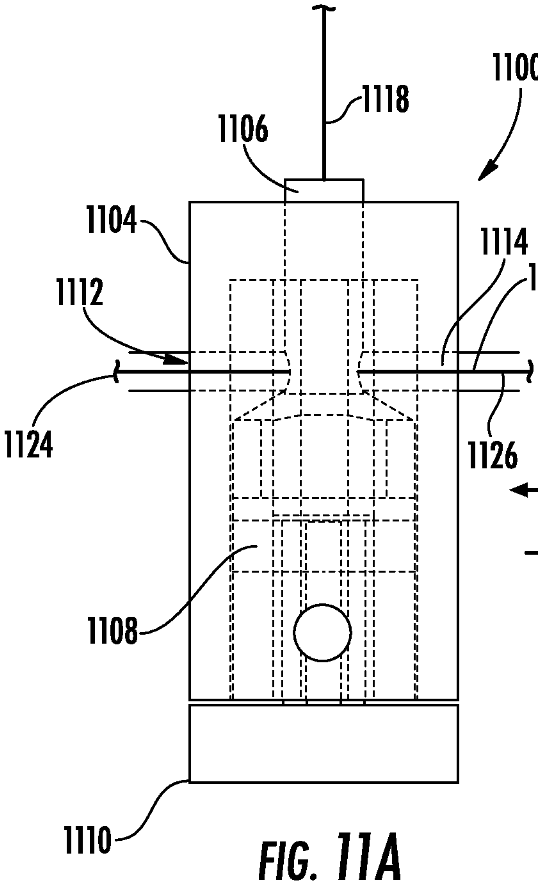
FIGS. 11A-11F are transparent views of spring-lock style locking portions according to embodiments of the present disclosure.
Figure 11B:
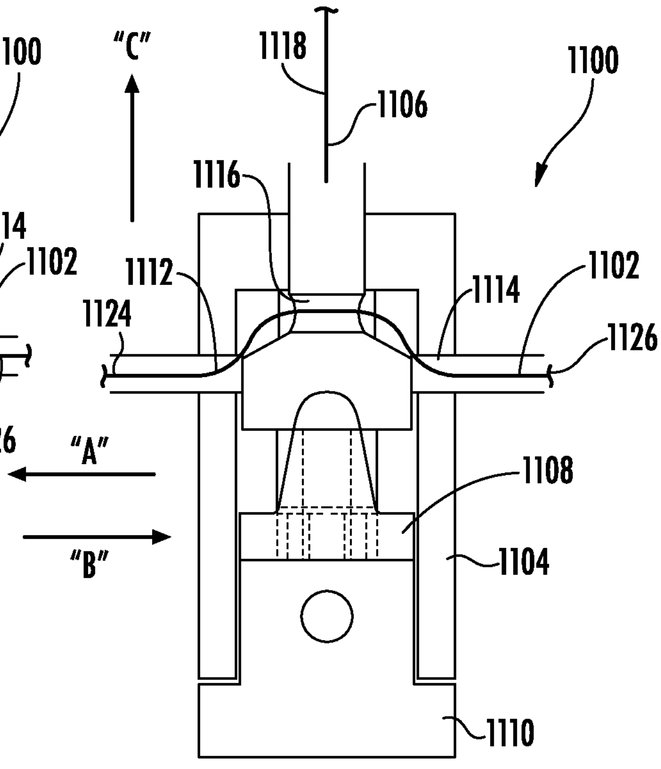
Figure 11C:
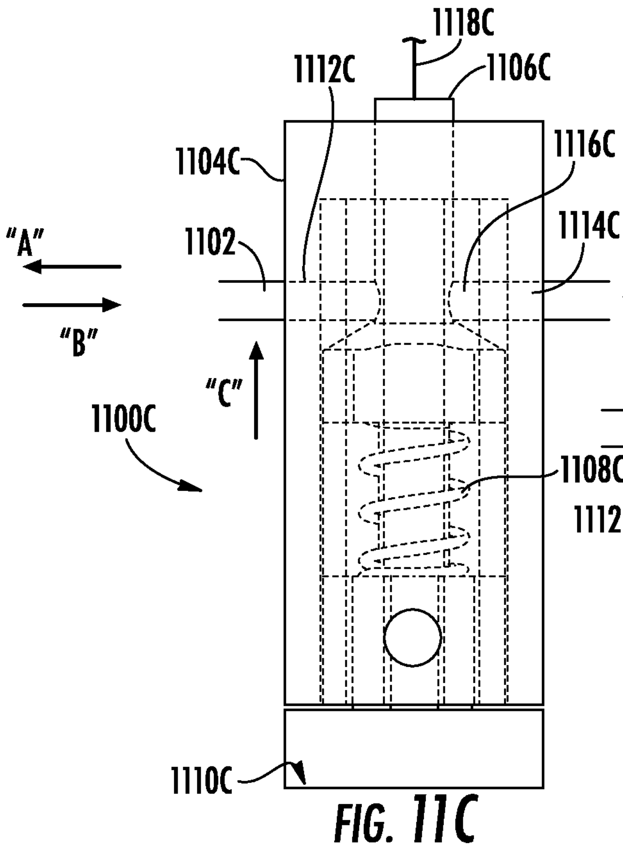
Figure 11D:
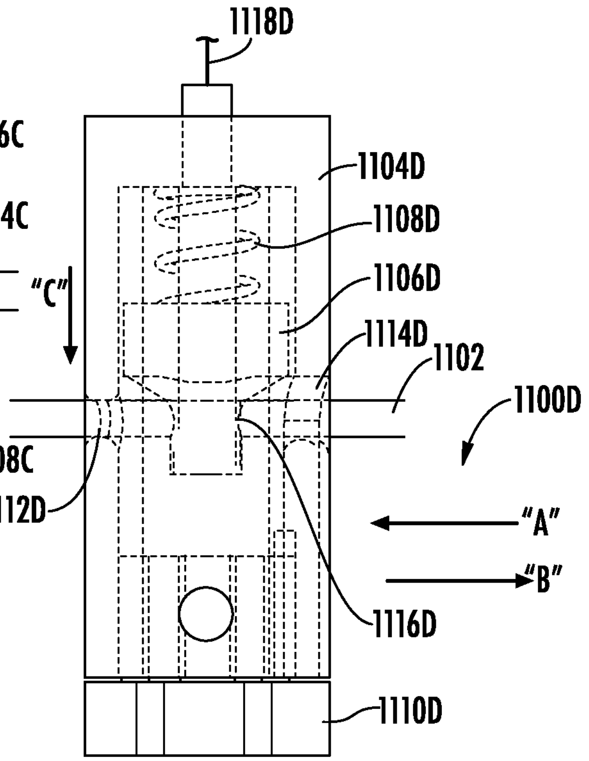
Figure 11E:
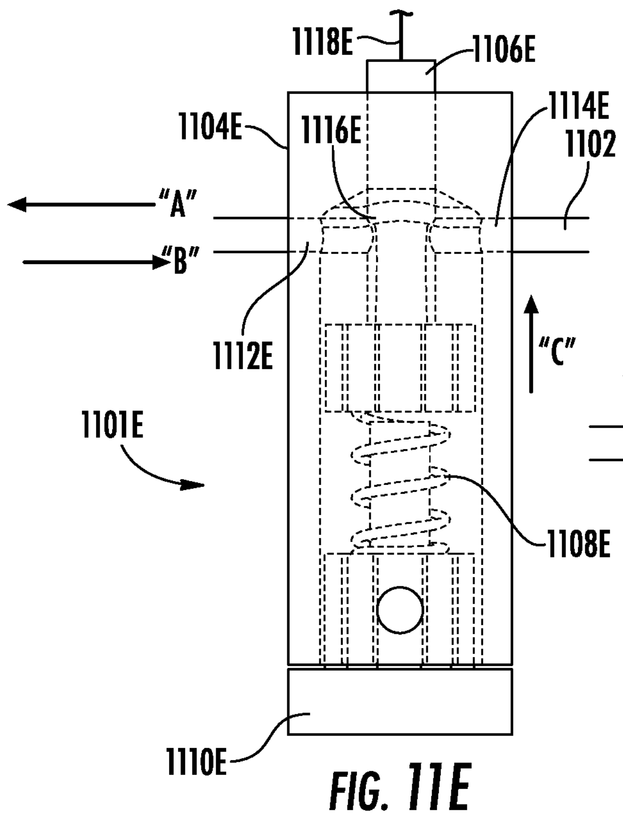
Figure 11F:
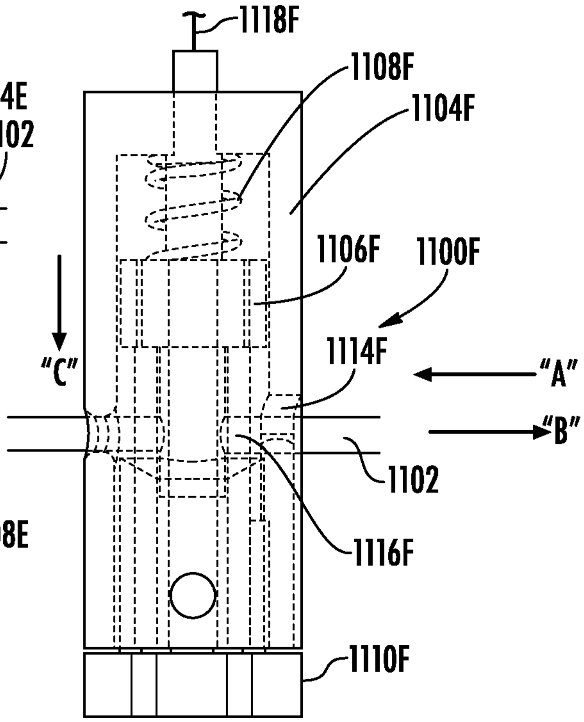

Referring now to FIGS. 11A and 11B, an embodiment of a locking portion 1100 for adjusting the tension of an artificial chordae tendineae 1102 according to the present disclosure is illustrated. The locking portion 1100 may be interchanged, as appropriate, with any of the locking portions disclosed in relation to the devices 300-600 of FIGS. 3A-6A. Thus, the locking portion 1100 may be combined with any of the a tissue-engaging portions, body portions and housing portions previously described in order to provide an anchor that includes features that enable a user to tension and/or de-tension as well as lock an artificial chordae tendineae between the anchor, which may be coupled to a papillary muscle or heart wall, and a clip, which may be coupled to a leaflet of a heart valve.

The artificial chordae tendineae is shown in FIGS. 11A, 11B as having a first end 1124 and a second end 1126. The first end 1124 may, in some embodiments, be coupled to a control filament (not shown) that runs through the catheter to a location in which a user can manipulate the position of (e.g., move) the artificial chordae tendineae 1102. In some embodiments the first end 1124 may include a loop or other connection mechanism through which the control filament may be coupled. Upon completion of the tensioning procedure, the control filament may be detached from the first end 1124 and removed via the catheter.

The locking portion 1100 may comprise a body portion 1104, a plunger 1106, a spring member 1108, and an end cap 1110. In the illustrated embodiment, the spring member 1108 may be made from silicone or other compressible material. The spring member may be molded to a shape that resiliently engages the plunger 1106 to bias the locking portion 1100 into a locked position. Due to the compressibility of the spring member 1108, application of force to the plunger 1106 can compress the spring member 1108 to move the locking portion 1100 from the locked position to an unlocked position. The body portion 1104 may include first and second lateral openings 1112, 1114 for receiving the artificial chordae tendineae 1102 therethrough. The plunger 1106 may include an opening 1116 for receiving the artificial chordae tendineae 1102 therethrough.

FIG. 11A shows the locking portion 1100 illustrated in the unlocked configuration, in which the first and second lateral openings 112, 114 are aligned with the opening 1116 in the plunger 1106. This may allow the artificial chordae tendineae 1102 to move with respect to the locking portion in either of the first and second directions (arrows "A", "B"). By contrast, FIG. 11B shows the locking portion 1100 in the locked configuration, in which the plunger 1106 is moved in the direction of arrow "C" so that the opening 1116 is out of alignment with the first and second lateral openings 1112, 1114 of the body portion 1104. Such an arrangement may pinch the artificial chordae tendineae 1102 between the surfaces of the plunger and the body portion, preventing the artificial chordae tendineae from moving with respect to the locking portion in either of the first and second directions (arrows "A" and "B"). In some embodiments the end cap 1110 may provide a fixed surface against which the spring member 1108 can press to bias the plunger 1106 in the direction of arrow "C" so that the locking portion 1100 is biased in the locked configuration of FIG. 11B. An actuator 1118 may be coupled to the plunger 1106 to enable a user to move the plunger from the configuration shown in FIG. 11B (locked) to the configuration shown in FIG. 11A (unlocked). For example, a user may apply a force to the actuator 1118 which in turn applies a force against the plunger 1106 to move in the direction opposite that of arrow "C" may overcome the bias of the spring member 1108. The plunger 1106 may be moved so that the opening 1116 is aligned with the first and second lateral openings 1112, 1114 of the body portion 1104, such that the artificial chordae tendineae 1102 can move in either the first or second directions.

In some embodiments, moving the artificial chordae tendineae 1102 in the direction of arrow "A" will tend to increase tension between the artificial chordae tendineae and the leaflet 150 (FIG. 2) of the heart valve. Where the locking portion 1100 is incorporated into a device that is coupled to a papillary muscle or heart wall 152, a target tension may be achieved in the artificial chordae tendineae 1102 to achieve a target effect on regurgitation of blood through the heart valve. Observation of regurgitation may be observed via transesophageal echocardiogram, fluoroscopy, or the like to determine whether a target affect has been achieved with the artificial chordae tendineae 1102 in place. If, upon observation, the user determines the tension in the artificial chordae tendineae 1102 is to be increased, the user may reconfigure the locking portion 1100 to assume the unlocked configuration (FIG. 11A) to allow the artificial chordae tendineae 1102 to be moved in the first direction (arrow "A") to increase tension in the artificial chordae tendineae.

If, upon observation, the user determines the tension in the artificial chordae tendineae 1102 is to be decreased, the artificial chordae tendineae may be moved in the second direction (arrow "B"). In such a case, the user may reconfigure the locking portion 1100 to assume the unlocked configuration (FIG. 11A) to allow the artificial chordae tendineae 1002 to move in the second direction (arrow "B") to reduce tension in the artificial chordae tendineae.

When a target reduced tension is achieved, the locking portion 1100 may be reconfigured to assume the locked configuration (FIG. 11B) to lock the artificial chordae tendineae 1102 to the locking portion 1100. This can be followed by additional observation of regurgitation, followed by additional tensioning/un-tensioning, and so on.

The actuator 1118 may run through a catheter to a location in which a user can actuate the actuator to "unlock" the locking portion 1100. Upon completion of the tensioning procedure, the actuator 1118 may be detached from the locking portion 1100 and may be removed via the catheter.

FIGS. 11C-F illustrate alternative embodiments of the concept described in relation to FIGS. 11A-B. Thus, each of these embodiments includes a body portion 1104C-F, a plunger 1106C-F, a spring member 1108C-F, and an end cap 1110C-F. The body portion 1104C-F4 may include first and second lateral openings 1112C-F, 1114C-F for receiving the artificial chordae tendineae 1102 therethrough. The plunger 1106C-F may include a corresponding opening 1116C-F for receiving the artificial chordae tendineae 1102 therethrough.

FIGS. 11C-F shows the locking portion 1100C-F in the unlocked configuration, which may allow the artificial chordae tendineae 1102 to move with respect to the locking portion in either of the first and second directions (arrows "A", "B"). In the locked configuration (not shown), the plunger 1106C-F is moved under the force of the spring member 1108C-F in the direction of arrow "C" so that the opening 1116C-F is out of alignment with the respective first and second lateral openings 1112C-F, 1114C-F of the body portion 1104C-F, which may pinch the artificial chordae tendineae 1102 between the surfaces of the plunger and the body portion, preventing the artificial chordae tendineae from moving with respect to the locking portion in either of the first and second directions (arrows "A" and "B"). In some embodiments the end cap 1110 may provide a fixed surface against which the spring member 1108C-F can press to bias the plunger 1106C-F in the direction of arrow "C" so that the locking portion 1100C-F is biased in the locked configuration. An actuator 1118C-F may be coupled to the plunger 1106 to enable a user to move the plunger from the locked configuration to the unlocked configuration by overcoming the bias of the spring member 1188C-F in the manner previously described in relation to FIGS. 11A and 11B. Adjustment of tension in the artificial chordae tendineae 1102 can proceed in the same manner as described in relation to FIGS. 11A and B.

Figure 12A:
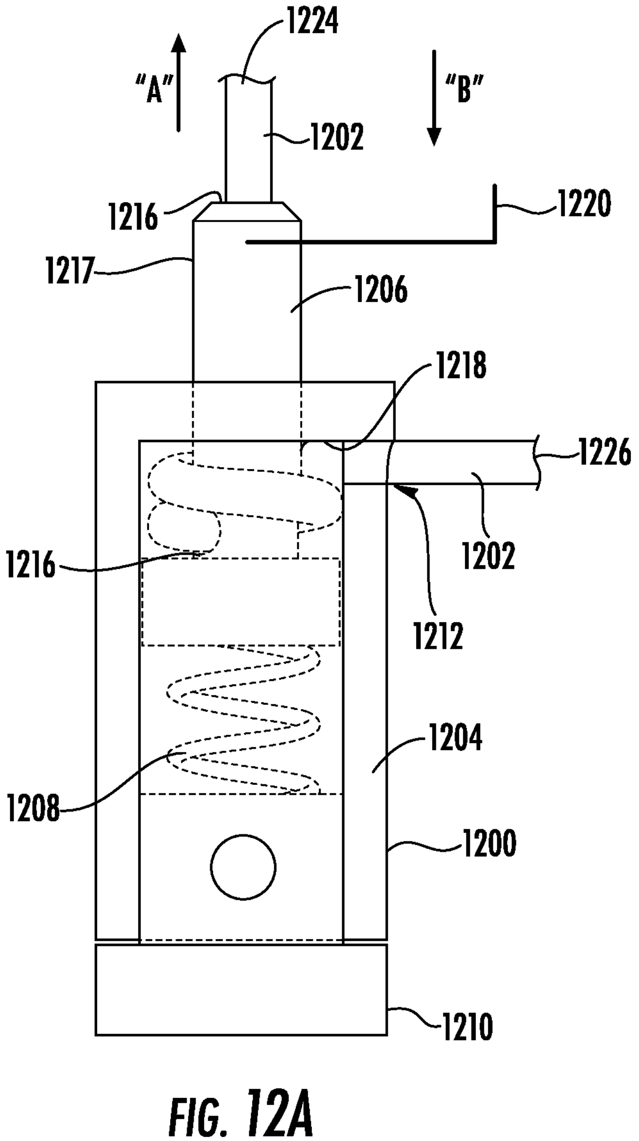
FIGS. 12A-B are transparent views of a plunger coil-lock style locking portion according to an embodiment of the present disclosure.
Figure 12B:
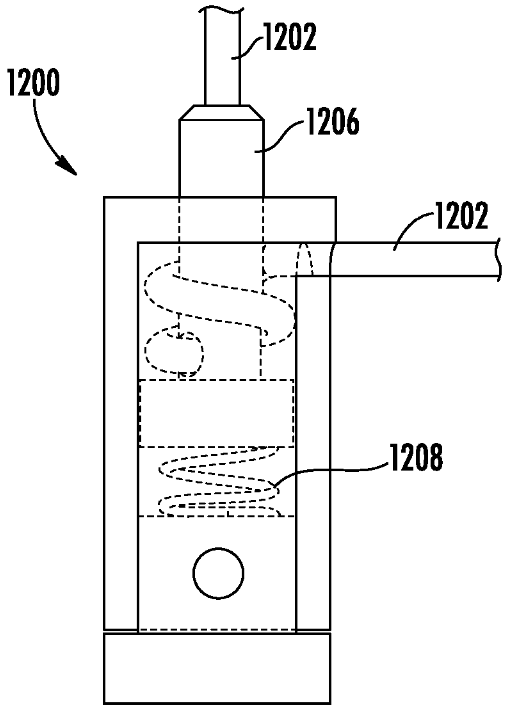

Referring now to FIGS. 12A and 12B, an embodiment of a locking portion 1200 for adjusting the tension of an artificial chordae tendineae 1202 according to the present disclosure is illustrated. The locking portion 1200 may be interchanged, as appropriate, with any of the locking portions disclosed in relation to the devices 300-600 of FIGS. 3A-6A. Thus, the locking portion 1200 may be combined with any of the a tissue-engaging portions, body portions and housing portions previously described in order to provide an anchor that includes features that enable a user to tension and/or de-tension as well as lock an artificial chordae tendineae between the anchor, which may be coupled to a papillary muscle or heart wall, and a clip, which may be coupled to a leaflet of a heart valve.

The artificial chordae tendineae is shown in FIG. 12A as having a first end 1224 and a second end 1226. The first end 1224 may, in some embodiments, be coupled to a control filament (not shown) that runs through the catheter to a location in which a user can manipulate the position of (e.g., move) the artificial chordae tendineae 1202. In some embodiments the first end 1224 may include a loop or other connection mechanism through which the control filament may be coupled. Upon completion of the tensioning procedure, the control filament may be detached from the first end 1224 and removed via the catheter.

The locking portion 1200 may comprise a body portion 1204, a plunger 1206, a spring member 1208 and an end cap 1210. The body portion 1204 may include a lateral opening 1212 for receiving the artificial chordae tendineae 1202 therethrough. The plunger 1206 may include a corresponding opening 1216 for receiving the artificial chordae tendineae 1202 therethrough and for directing the artificial chordae tendineae out through an upper end 1217 of the plunger.

FIG. 12A shows the locking portion 1200 in the locked configuration, which may prevent the artificial chordae tendineae 1202 from moving with respect to the locking portion in either of the first and second directions (arrows "A", "B"). In this configuration, the artificial chordae tendineae 1202 is pressed against an inner surface 1218 of the body portion 1204, which prevents the artificial chordae tendineae from moving with respect to the locking portion 1200 in either of the first and second directions (arrows "A" and "B"). In some embodiments the end cap 1210 may provide a fixed surface against which the spring member 1208 can press to bias the plunger 1206 in the direction of arrow "A" so that the locking portion 1200 is biased in the locked configuration of FIG. 12A. An actuator 1220 may be coupled to the plunger 1206 to move the plunger from the locked configuration shown in FIG. 12A to the unlocked configuration shown in FIG. 12B. For example, applying a force against the plunger 1206 via the actuator 1220 to move the plunger in the direction of arrow "B" may overcome the bias of the spring member 1208, moving the plunger so that the artificial chordae tendineae 1202 is no longer compressed between the plunger 1206 and the inner surface 1218 of the body portion 1204. In this unlocked configuration of FIG. 12B, the artificial chordae tendineae 1202 can be pulled through the locking portion 1200 to adjust the tension between an associated anchor and one or more leaflet clips 206 (FIG. 2).

In some embodiments, moving of the artificial chordae tendineae 1202 in the direction of arrow "A" will tend to increase tension between the artificial chordae tendineae and the leaflet 150 (FIG. 2) of the heart valve. Where the locking portion 1200 is incorporated into a device that is coupled to a papillary muscle or heart wall 152, a target tension may be achieved in the artificial chordae tendineae 1202 to achieve a target effect on regurgitation of blood through the heart valve. Observation of regurgitation may be observed via transesophageal echocardiogram, fluoroscopy, or the like to determine whether a target affect has been achieved with the artificial chordae tendineae 1202 in place. If, upon observation, the user determines the tension in the artificial chordae tendineae 1202 is to be increased, the user may reconfigure the locking portion 1200 to assume the unlocked configuration to allow the artificial chordae tendineae 1202 to be moved in the first direction to increase tension in the artificial chordae tendineae.

If, upon observation, the user determines the tension in the artificial chordae tendineae 1202 is to be decreased, the artificial chordae tendineae may be moved in the second direction (arrow "B"). In such a case, the user may reconfigure the locking portion 1200 to assume the unlocked configuration to allow the artificial chordae tendineae 1202 to move in the second direction (arrow "B") to reduce tension in the artificial chordae tendineae. When a target reduced tension is achieved, the locking portion 1200 may be reconfigured to assume the locked configuration to lock the artificial chordae tendineae 1202 to the locking portion 100. This can be followed by additional observation of regurgitation, followed by additional tensioning/un-tensioning, and so on.

The actuator 1220 may run through a catheter to a location in which a user can actuate the actuator to "unlock" the locking portion 1200. Upon completion of the tensioning procedure, the actuator 1220 may be detached from the locking portion 1200 and may be removed via the catheter.

Figure 13:
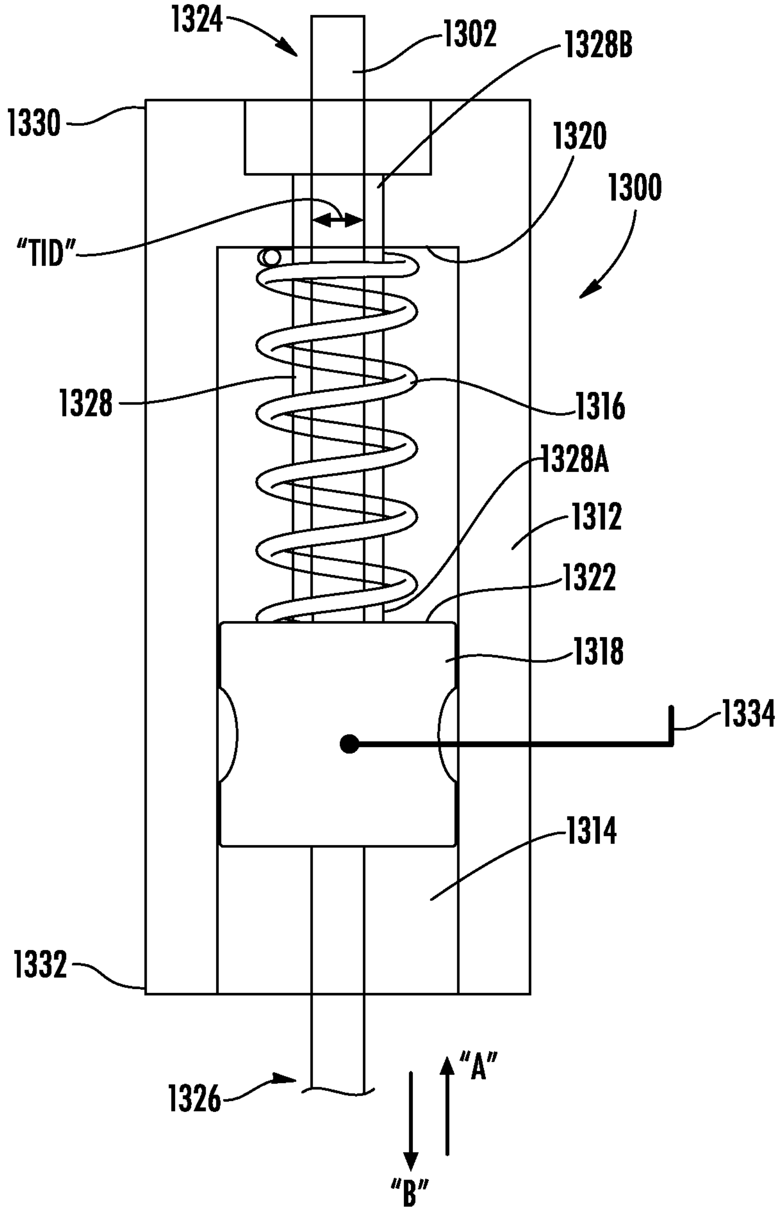
FIG. 13 is a transparent view of a sleeve-lock style locking portion according to an embodiment of the present disclosure.

Referring now to FIG. 13, an embodiment of a locking portion 1300 for adjusting the tension of an artificial chordae tendineae 1302 according to the present disclosure is illustrated. The locking portion 1300 may be interchanged, as appropriate, with any of the locking portions disclosed in relation to the devices 300-600 of FIGS. 3A-6A. Thus, the locking portion 1300 may be combined with any of the a tissue-engaging portions, body portions, and housing portions previously described in order to provide an anchor that includes features that enable a user to tension and/or de-tension as well as lock an artificial chordae tendineae between the anchor, which may be coupled to a papillary muscle or heart wall, and a clip, which may be coupled to a leaflet of a heart valve.

The artificial chordae tendineae is shown in FIG. 13 as having a first end 1324 and a second end 1326. The first end 1324 may, in some embodiments, be coupled to a control filament (not shown) that runs through the catheter to a location in which a user can manipulate the position of (e.g., move) the artificial chordae tendineae 1302. In some embodiments the first end 1324 may include a loop or other connection mechanism through which the control filament may be coupled. Upon completion of the tensioning procedure, the control filament may be detached from the first end 1324 and removed via the catheter. The second end 1326 of the artificial chordae tendineae 1302 may extend within the heart to couple directly or indirectly to one or more leaflet clips 206 (FIG. 2). In some embodiments the second end 1326 may couple to a filament 200 (FIG. 2) that, in turn, couples to one or more leaflet clips 206.

In the illustrated embodiment the locking portion 1300 comprises a housing portion 1312 having a longitudinal opening 1314 within which a spring element 1316 and a plunger 1318 are disposed. The spring element 1316 may be disposed between a shoulder 1320 of the housing portion and a face 1322 of the plunger 1318 to bias the plunger away from the shoulder. The spring element and the plunger can be movable within the longitudinal opening 1314. A tube element 1328 may be disposed within the spring element 1316 and may have a first end 1328A coupled to the plunger 1318 and a second end 1328B coupled to the housing portion near a first end 1330 of the locking portion 1300. In one non-limiting example embodiment the tube element 1328 is formed from an elastic material such as silicone. A portion of the artificial chordae tendineae 1302 may be disposed within the tube element 1328 such that the first end of the artificial chordae tendineae extends from the first end 1330 of the locking portion 1300 and the second end extends from the second end 1332 of the locking portion.

The tube element 1328 may be configured such that its inner diameter "TID", in an unlocked configuration, is sized to allows the artificial chordae tendineae 1302 to move in the first and second directions (arrows "A" and "B" respectively). The tube element 1328 may be configurable to assume a locked configuration in which the inner diameter "TID" is reduced such that it squeezes the artificial chordae tendineae 1302 to prevent the artificial chordae tendineae from moving with respect to the tube element. In some embodiments the tube element 1328 is moved to the locked configuration by moving the first end 1328A of the tube element in the second direction (arrow "B"), and the tube element is moved to the unlocked configuration by moving the first end of the tube element in the first direction (arrow "A").

FIG. 13 illustrates the locking portion 1300 (and tube element 1328) in the locked configuration, in which the spring element 1316 applies a bias move the plunger 1318 toward the second end 1332 of the housing portion 1312 (i.e., in the second direction (arrow "B")). This extends the tube element 1328 so that its inner diameter "TID" presses tightly against the artificial chordae tendineae to create a frictional lock, preventing the artificial chordae tendineae 1302 from moving through the locking portion.

An actuator 1334 may be coupled to the plunger 1318 to selectively move the plunger toward the first end 1330 of the housing portion 1312 (i.e., in the first direction (arrow "A"), so that the inner diameter "TID" relieves force from the artificial chordae tendineae, reducing friction to allow the artificial chordae tendineae 1302 to move through the locking portion 1300. In some embodiments, the actuator 1334 (or a separate member coupled to the actuator) may extend through a catheter so that a user can manually adjust the actuator to move the locking portion 1300 between the locked and unlocked configurations from a location outside the patient's body.

The actuator 1334 may be movable in the first and second directions (arrows "A" and "B", respectively) to move the plunger 1318 and the tube element 1328 between the locked and unlocked configurations. When the tube element 1328 is in the unlocked configuration, the artificial chordae tendineae 1302 can be moved in the first direction (arrow "A") or the second direction (arrow "B"). When the tube element 1328 is in the locked configuration, the artificial chordae tendineae is prevented from moving in either the first direction (arrow "A") or the second direction (arrow "B").

In some embodiments, moving the artificial chordae tendineae 1302 in the direction of arrow "A" will tend to increase tension between the artificial chordae tendineae and the leaflet 150 (FIG. 2) of the heart valve. Adjusting the tension in the artificial chordae tendineae 1302 may achieve a target effect on regurgitation of blood through the heart valve. Observation of regurgitation may be observed via transesophageal echocardiogram, fluoroscopy, or the like to determine whether a target affect has been achieved with the artificial chordae tendineae 1302 in place. If, upon observation, the user determines the tension in the artificial chordae tendineae 1302 is to be increased, the user may move the actuator 1334 in the first direction (arrow "A") to release the artificial chordae tendineae 1302 from the frictional lock within the tube element 1328. The user may then apply additional tension to the artificial chordae tendineae (using, for example, a control filament manipulatable from a proximal end of a catheter) to move it further in the first direction (arrow "A"). When a target tension is achieved, the actuator 1334 may be moved in the second direction (arrow "B") by an amount to lock the artificial chordae tendineae 1302 within the tube element 1328. This can be followed by additional observation of regurgitation, followed by additional tensioning, and so on.

If, upon observation, the user determines the tension in the artificial chordae tendineae 1302 is to be decreased, the artificial chordae tendineae may be moved in the second direction (arrow "B"). In such a case, the user may move the actuator 1334 in the first direction (arrow "A") to release the artificial chordae tendineae 1302 from the frictional lock within the tube element 1328, and may reduce tension in the artificial chordae tendineae to move it further in the first direction (arrow "A"). When a target reduced tension is achieved, the actuator 1334 may be moved in the second direction (arrow "B") by an amount to lock the artificial chordae tendineae 1302 within the tube element 1328. This can be followed by additional observation of regurgitation, followed by additional tensioning/un-tensioning, and so on.

Upon completion of the tensioning procedure, the actuator 1334 may be locked to the housing portion by, for example, crimping, cutting and bonding, swaging or other mechanical technique. The remaining portion of the actuator 1334 (i.e., the portion residing in the catheter) may be disconnected and removed via the catheter. The control filament can similarly be decoupled from the first end 1324 of the artificial chordae tendineae 1302 and removed via the catheter.

Figure 14:
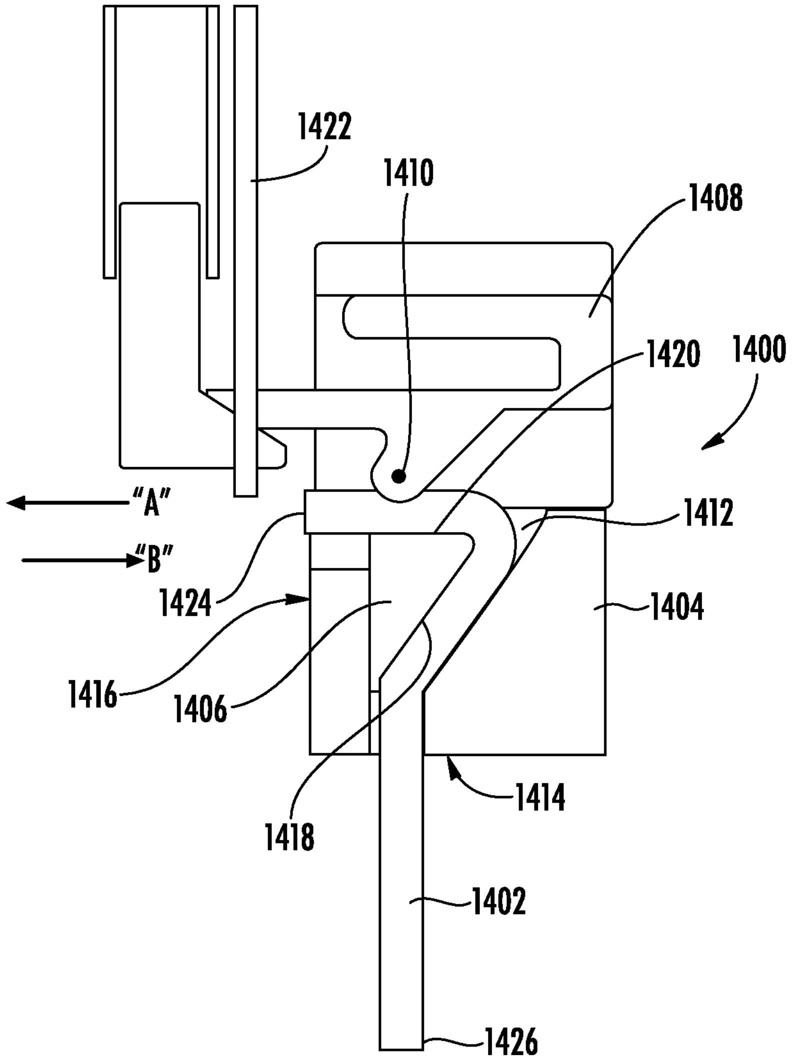
FIG. 14 is a cross-section view of a spring wedge-lock style locking portion according to an embodiment of the present disclosure.

Referring now to FIG. 14, an embodiment of a locking portion 1400 for adjusting the tension of an artificial chordae tendineae 1402 according to the present disclosure is illustrated. The locking portion 1400 may be interchanged, as appropriate, with any of the locking portions disclosed in relation to the devices 300-600 of FIGS. 3A-6A. Thus, the locking portion 1400 may be combined with any of the a tissue-engaging portions, body portions and housing portions previously described in order to provide an anchor that includes features that enable a user to tension and/or detension as well as lock an artificial chordae tendineae between the anchor, which may be coupled to a papillary muscle or heart wall, and a clip, which may be coupled to a leaflet 150 (FIG. 2) of a heart valve.

The locking portion 1400 may include a housing portion 1404 that receives a floating block portion 1406 and a locking element 1408. The floating block portion 1406 may have a triangular shape and may be movable within the housing portion 1404. The locking element 1408 may likewise be movable within the housing portion 1404 and may include a protrusion 1410 oriented toward a first side of the floating block portion 1406.

The housing portion 1404 may also include a groove 1412 for guiding the artificial chordae tendineae from a first side 1414 of the housing portion to a second side 1416 of the housing portion. The groove 1412 may be configured to guide the artificial chordae tendineae against the hypotenuse side 1418 of the floating block portion 1406, and then against a second side 1420 of the floating block portion. Thus, the groove 1412 may guide the artificial chordae tendineae 1402 around two sides of the floating block portion 1406 and then to direct the artificial chordae tendineae out of the housing portion 1404.

The locking element 1408 may be positioned so that the protrusion 1410 can engage the artificial chordae tendineae 1402 to press it against the second side 1420 of the floating block portion 1406. At the same time, the protrusion 1410 forces the floating block portion 1406 down so that the hypotenuse side 1418 of the floating block portion presses the artificial chordae tendineae 1402 against an opposing surface of the groove 1412. The movements of these elements lock the artificial chordae tendineae to the locking portion 1400 so that the artificial chordae tendineae is prevented from moving in the first direction and the second direction. This locked configuration is shown in FIG. 14.

An actuator 1422 may be coupled to the locking element 1408 to move the protrusion 1410 away from the artificial chordae tendineae 1402 so that the artificial chordae tendineae is permitted to move in the first and second directions (arrows “A” and “B” respectively). In some embodiments, the actuator 1422 (or a separate member coupled to the actuator) may extend through a catheter so that a user can manually adjust the actuator to move the locking portion 1400 between the locked and unlocked configurations from a location outside the patient’s body.

In some embodiments, moving the artificial chordae tendineae 1402 in the direction of arrow “A” will tend to increase tension between the artificial chordae tendineae and the leaflet 150 (FIG. 2) of the heart valve. Adjusting the tension in the artificial chordae tendineae 1402 may achieve a target effect on regurgitation of blood through the heart valve. Observation of regurgitation may be observed via transesophageal echocardiogram, fluoroscopy, or the like to determine whether a target affect has been achieved with the artificial chordae tendineae 1402 in place. If, upon observation, the user determines the tension in the artificial chordae tendineae 1402 is to be increased, the user may move the actuator 1422 so that the protrusion 1410 moves away from the artificial chordae tendineae to allow the artificial chordae tendineae to move. The user may then apply additional tension to the artificial chordae tendineae 1402 (using, for example, a control filament manipulatable from a proximal end of a catheter) to move it further in the first direction (arrow “A”). When a target tension is achieved, the actuator 1422 may be moved to thereby move the protrusion 1410 toward the artificial chordae tendineae to lock the artificial chordae tendineae between the protrusion and the block portion 1406. This can be followed by additional observation of regurgitation, followed by additional tensioning, and so on.

If, upon observation, the user determines the tension in the artificial chordae tendineae 1402 is to be decreased, the artificial chordae tendineae may be moved in the second direction (arrow “B”). In such a case, the user may move the actuator 1422 to release the artificial chordae tendineae 1402 from between the protrusion 1410 and the block portion 1406, and may reduce tension in the artificial chordae tendineae to move it further in the second direction (arrow “B”). When a target reduced tension is achieved, the actuator 1422 may be moved so that the protrusion 1410 engages the artificial chordae tendineae 1402 to prevent further movement. This can be followed by additional observation of regurgitation, followed by additional tensioning/un-tensioning, and so on.

Upon completion of the tensioning procedure, the actuator 1422 may be locked to the housing portion by, for example, crimping, cutting and bonding, swaging or other mechanical technique. The remaining portion of the actuator 1422 (i.e., the portion residing in the catheter) may be disconnected and removed via the catheter. The control filament can similarly be decoupled from a first end 1424 of the artificial chordae tendineae 1402 and removed via the catheter. A second end 1426 of the artificial chordae tendineae 1402 may extend within the heart to couple directly or indirectly to one or more leaflet clips 206 (FIG. 2). In some embodiments the second end 1426 may couple to a filament 200 (FIG. 2) that, in turn, couples to one or more leaflet clips 206

Figure 15A:
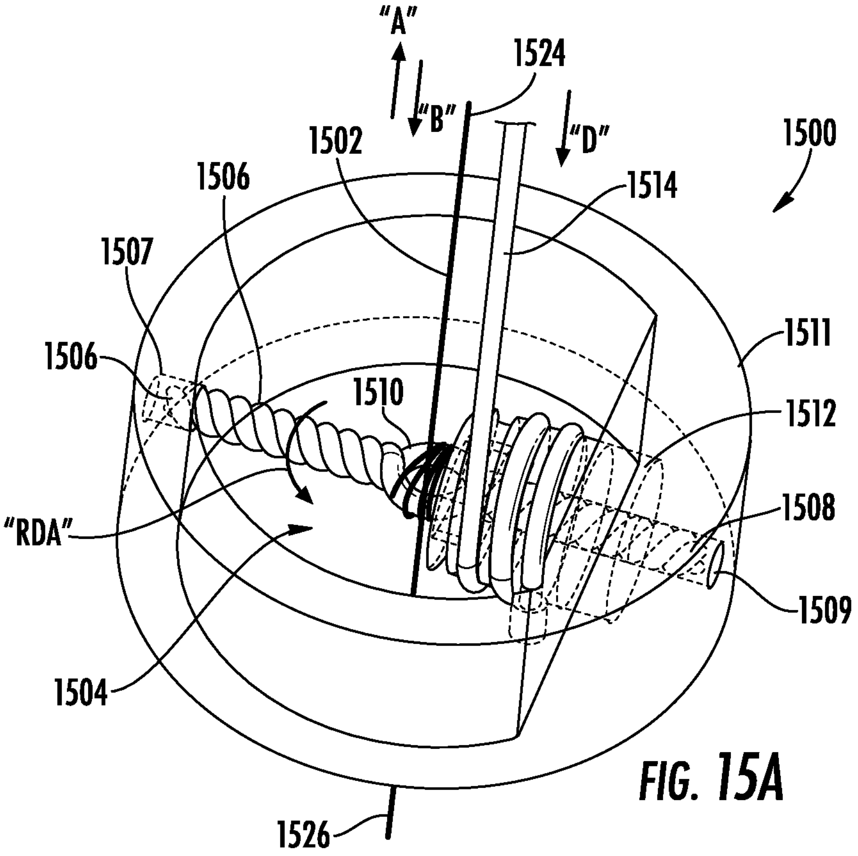
FIGS. 15A and 15B are perspective views of a spring wind-lock style locking portion according to an embodiment of the present disclosure.
Figure 15B:
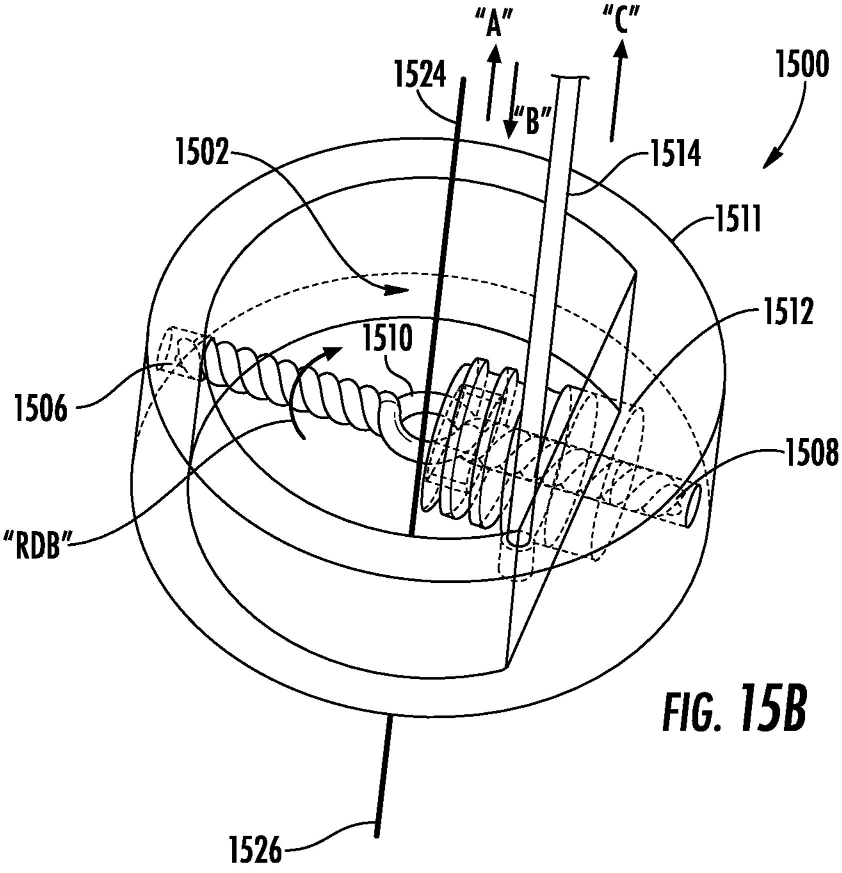

Referring now to FIGS. 15A and 15B, an embodiment of a locking portion 1500 for adjusting the tension of an artificial chordae tendineae 1502 according to the present disclosure is illustrated. The locking portion 1500 may be interchanged, as appropriate, with any of the locking portions disclosed in relation to the devices 300-600 of FIGS. 3A-6A. Thus, the locking portion 1500 may be combined with any of the a tissue-engaging portions, body portions and housing portions previously described in order to provide an anchor that includes features that enable a user to tension and/or de-tension as well as lock an artificial chordae tendineae between the anchor, which may be coupled to a papillary muscle or heart wall, and a clip, which may be coupled to a leaflet of a heart valve.

The artificial chordae tendineae is shown in FIGS. 15A, 15B as having a first end 1524 and a second end 1526. The first end 1524 may, in some embodiments, be coupled to a control filament (not shown) that runs through the catheter to a location in which a user can manipulate the tension in the artificial chordae tendineae 1502. In some embodiments the first end 1524 may include a loop or other connection mechanism through which the control filament may be coupled. Upon completion of the tensioning procedure, the control filament may be detached from the first end 1524 and removed via the catheter. The second end 1526 of the artificial chordae tendineae 1502 may extend within the heart to couple directly or indirectly to one or more leaflet clips 206 (FIG. 2). In some embodiments the second end 1526 may couple to a filament 200 (FIG. 2) that, in turn, couples to one or more leaflet clips 206.

The locking portion 1500 may comprise a coil spring element 1504 having first and second spring ends 1506, 1508 and a central ring portion 1510 through which the artificial chordae tendineae 1502 is disposed. The first and second spring ends 1506, 1508 may be fixed within respective first and second recesses 1507, 1509 in a body portion 1511 of the locking portion 1500. An actuator 1512 may be coupled to a portion of the central ring portion 1510 so that the central ring portion can be rotated by rotating the actuator. The actuator 1512 may be coupled to a control element 1514 such as a filament manipulatable from a proximal end of a catheter so that when the control element is moved, the actuator and the central ring portion 1510 are rotated.

The coil spring element 1504 may be naturally biased to twist in either a first rotational direction (arrow “RDA”) or a second rotational direction (arrow “RDB”). In the illustrated embodiment, the coil spring element 1504 is biased to twist in the first rotational direction (“RDA”) so that the resting state of the spring is associated with a locked configuration of the locking portion 1500 (FIG. 15A). In the locked configuration, the artificial chordae tendineae 1502 is wrapped around the central ring portion 1510, preventing the artificial chordae tendineae from moving in the first or second directions “A”, “B”.

To move the locking portion 1500 to the unlocked configuration (FIG. 15B), the control element 1514 can be moved in an actuation direction (arrow “C”). This movement causes the actuator 1512 and the central ring portion 1510 to rotate in the second rotational direction "RDB", which unwraps the artificial chordae tendineae 1502 from the central ring portion until the artificial chordae tendineae runs straight through the central ring portion as shown in FIG. 15B.

In some embodiments, moving the artificial chordae tendineae 1502 in the direction of arrow "A" will tend to increase tension between the artificial chordae tendineae and the leaflet 150 (FIG. 2) of the heart valve. Adjusting the tension in the artificial chordae tendineae 1502 may achieve a target effect on regurgitation of blood through the heart valve. Observation of regurgitation may be observed via transesophageal echocardiogram, fluoroscopy, or the like to determine whether a target affect has been achieved with the artificial chordae tendineae 1502 in place. If, upon observation, the tension in the artificial chordae tendineae 1502 is to be increased, the coil spring element 1504 may be rotated in the first or second direction ("RDA", "RDB") as appropriate to allow the artificial chordae tendineae 1502 to pass therethrough. The user may then apply additional tension to the artificial chordae tendineae 1502 (using, for example, a control filament manipulatable from a proximal end of a catheter) to move it further in the first direction (arrow "A"). When a target tension is achieved, the coil spring element 1504 may be rotated in the first or second direction ("RDA", "RDB") as appropriate to pinch the artificial chordae tendineae to prevent further movement of the artificial chordae tendineae in the first or second directions (arrows "A" and "B" respectively). This can be followed by additional observation of regurgitation, followed by additional tensioning, and so on.

If, upon observation, the user determines the tension in the artificial chordae tendineae 1502 is to be decreased, the artificial chordae tendineae may be moved in the second direction (arrow "B"). In such a case, locking portion 1500 may be moved to the unlocked configuration as previously described, the user may then reduce tension in the artificial chordae tendineae to move it further in the second direction (arrow "B"). When a target reduced tension is achieved, the locking portion 1500 can be returned to the locked configuration as previously described to prevent further movement. This can be followed by additional observation of regurgitation, followed by additional tensioning/un-tensioning, and so on.

Figure 16A:
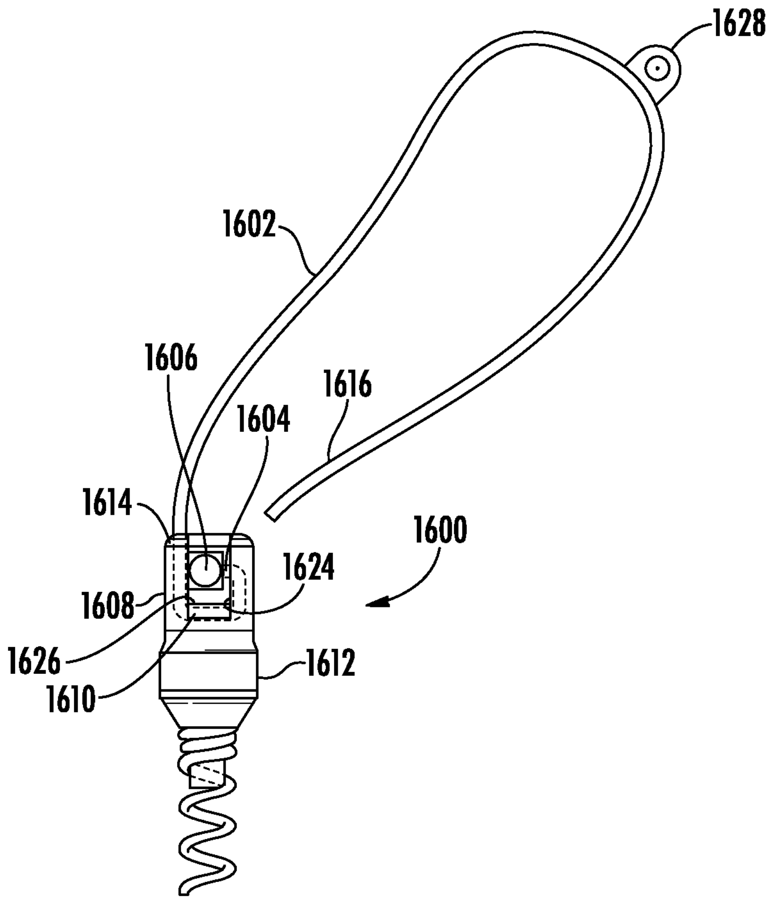
FIGS. 16A and 16B are perspective views of a suture-lock style locking portion according to an embodiment of the present disclosure.
Figure 16B:
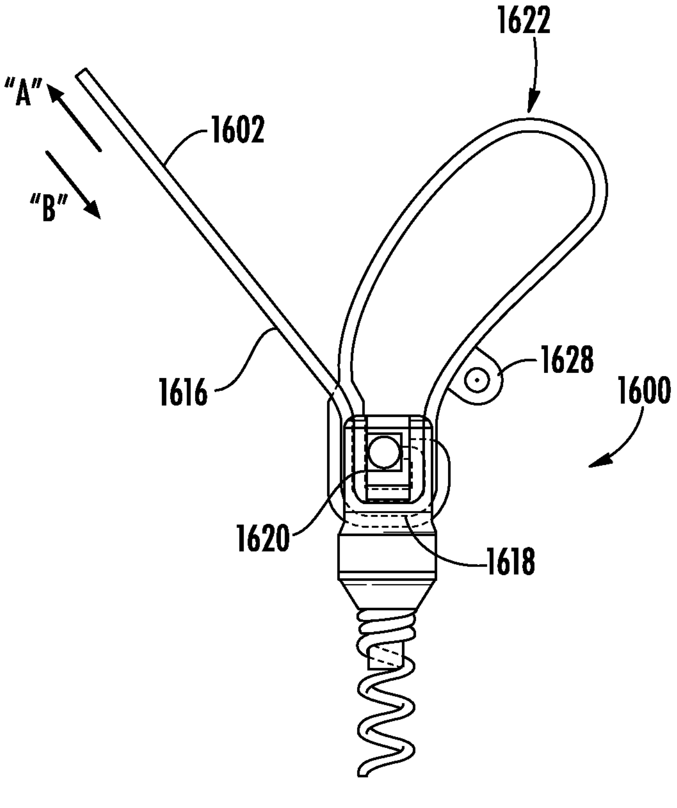

Referring now to FIGS. 16A and 16B, an embodiment of a locking portion 1600 for adjusting the tension of an artificial chordae tendineae 1602 according to the present disclosure is illustrated. The locking portion 1600 may be interchanged, as appropriate, with any of the locking portions disclosed in relation to the devices 300-600 of FIGS. 3A-6A. Thus, the locking portion 1600 may be combined with any of the a tissue-engaging portions, body portions, and housing portions previously described in order to provide an anchor that includes features that enable a user to tension and/or de-tension as well as lock an artificial chordae tendineae between the anchor, which may be coupled to a papillary muscle or heart wall, and a clip, which may be coupled to a leaflet of a heart valve.

The locking portion 1600 may be coupled to a first end 1604 of the artificial chordae tendineae 1602. In one embodiment, the first end 1604 is knotted or otherwise fixed to a protrusion 1606 in a body portion 1608 of the locking portion 1600. A portion of the artificial chordae tendineae 1602 may be disposed in a recess 1610 within the body portion 1612 and may exit through an upper surface 1614 of the locking portion.

As shown in FIG. 16B, a second end 1616 of the artificial chordae tendineae 1602 may be strung inside of itself and around respective bottom and side portions 1618, 1620 of the recess 1610 within the body portion 1612, such that the second end may extend away from the locking portion 1600. In some embodiments, the artificial chordae tendineae 1602 comprises multiple filaments (e.g., it may be braided or stranded) to enable it to be strung inside of itself in the aforementioned manner. As shown in FIG. 16B, the artificial chordae tendineae 1602 can thus form a loop 1622 that is couplable, directly or indirectly, to one or more leaflet clips 206 (FIG. 2). The second end 1616 of the artificial chordae tendineae 1602 may be coupled to a filament disposed in or on a catheter so that a user can manipulate the artificial chordae tendineae 1602 by applying a force to the filament. Alternatively, the second end 1616 of the artificial chordae tendineae 1602 may itself be disposed through the catheter so that the user can directly manipulate the second end.

The artificial chordae tendineae 1602 can be moved in a first direction (arrow "A") upon application of force to the second end 1616 of the artificial chordae tendineae (or a filament attached thereto). The friction resulting from the artificial chordae tendineae 1602 being strung inside itself, along with the interaction of the artificial chordae tendineae with corner portions 1624, 1626 bordering the recess 1610 of the locking portion 1600, however, prevent reverse movement of the artificial chordae tendineae in the second direction (arrow "B").

To unlock the locking portion 1600 (i.e., to allow the artificial chordae tendineae 1602 to move in the second direction "B"), a force can be applied to an eyelet 1628 coupled to the artificial chordae tendineae 1602 directly adjacent to the locking portion. A separate control element (e.g., filament) may be coupled to the eyelet 1628 so that a user can unlock the locking portion 1600 by applying a force to the separate control filament. Application of force to the eyelet in this manner can overcome the frictional and other forces tending to prevent movement in the second direction (arrow "B).

In some embodiments, moving the artificial chordae tendineae 1602 in the direction of arrow "A" will tend to increase tension between the artificial chordae tendineae and the leaflet 150 (FIG. 2) of the heart valve. Adjusting the tension in the artificial chordae tendineae 1602 may achieve a target effect on regurgitation of blood through the heart valve. Observation of regurgitation may be observed via transesophageal echocardiogram, fluoroscopy, or the like to determine whether a target affect has been achieved with the artificial chordae tendineae 1602 in place. If, upon observation, the user determines the tension in the artificial chordae tendineae 1602 is to be increased, a force may be applied to the second end 1616 (or filament attached thereto) to move the artificial chordae tendineae in the first direction (arrow "A") to apply additional tension to the artificial chordae tendineae 1602. This can be followed by additional observation of regurgitation, followed by additional tensioning, and so on.

If, upon observation, the user determines the tension in the artificial chordae tendineae 1602 is to be decreased, the artificial chordae tendineae may be moved in the second direction (arrow "B") by applying force to the eyelet 1628. This can be followed by additional observation of regurgitation, followed by additional tensioning/un-tensioning, and so on.

All the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system for adjusting tension in an artificial chordae tendineae, the system comprising:
- a clip engageable with a leaflet of a heart valve;
- an anchor engageable with a papillary muscle or heart wall; and
- an artificial chordae tendineae coupleable between said clip and said anchor;
- wherein said anchor includes:
- a body portion; and
- a locking portion engageable with said artificial chordae tendineae and configured to allow movement of said artificial chordae tendineae in a first direction with respect to said body portion, while preventing movement of said artificial chordae tendineae in a second direction opposite the first direction;
- said system further comprises an actuator coupled to said locking portion to move a portion of said locking portion in the first direction to enable selective movement of said artificial chordae tendineae in the second direction; and
- wherein the actuator is a filament extending proximally to a user so that the user can activate said actuator to release said locking portion by pulling said actuator.

2. The system of claim 1, wherein:
- said body portion defines a longitudinal slot therethrough, said artificial chordae tendineae extending through the slot; and
- said locking portion comprises a locking element movable within the longitudinal slot in said body portion between a position contacting said artificial chordae tendineae to allow said artificial chordae tendineae to move in the first direction, and a position preventing said artificial chordae tendineae from moving in the second direction.

3. The system of claim 2, wherein said locking element presses said artificial chordae tendineae against a wall of said body portion to prevent said artificial chordae tendineae from moving in the second direction.

4. The system of claim 1, wherein said locking portion includes a locking element positioned with respect to said body portion and said artificial chordae tendineae to prevent movement of said artificial chordae tendineae in the second direction.

5. The system of claim 4, wherein said locking element is movable in the first direction to allow movement of said artificial chordae tendineae with respect to said housing in the first direction.

6. The system of claim 4, wherein said locking element is configured and positioned to press said artificial chordae tendineae into engagement with a portion of said body portion to prevent movement of said artificial chordae tendineae in the second direction.

7. The system of claim 1, wherein said locking portion includes a locking element movable in the first direction with said artificial chordae tendineae to allow movement of said artificial chordae tendineae, and movable with said artificial chordae tendineae in the second direction to prevent further movement of said artificial chordae tendineae in the second direction.

8. The system of claim 1, wherein said locking portion includes a locking element movable with respect to said body portion, and said actuator is coupled to said locking element of said locking portion.

9. A device for adjusting tension in an artificial chordae tendineae, the device comprising:
- a body portion;
- a locking portion configured and positioned with respect to said body portion to allow movement of an artificial chordae tendineae in a first direction with respect to said body portion, while preventing movement of the artificial chordae tendineae in a second direction opposite the first direction;
- an actuator coupled to said locking portion to move a portion of said locking portion in the first direction to enable selective movement of the artificial chordae tendineae in the second direction; and
- wherein the actuator is a filament extending proximally to a user so that the user can activate said actuator to release said locking portion by pulling said actuator.

10. The device of claim 9, wherein:
- said body portion defines a longitudinal slot therethrough for passage of an artificial chordae tendineae therethrough; and
- said locking portion further comprises a locking element movable within the longitudinal slot in said body portion between a position contacting an artificial chordae tendineae extending through the longitudinal slot to allow the artificial chordae tendineae to move in the first direction, and a position preventing the artificial chordae tendineae from moving in the second direction.

11. The device of claim 10, wherein said locking element is positioned with respect to the longitudinal slot and said body portion to press an artificial chordae tendineae against a wall of said body portion to prevent the artificial chordae tendineae from moving in the second direction.

12. The device of claim 9, wherein said locking portion includes a locking element positioned with respect to said body portion to prevent movement of an artificial chordae tendineae with respect to said body portion in the second direction.

13. The device of claim 12, wherein said locking element is movable in the first direction to allow movement of an artificial chordae tendineae with respect to said housing in the first direction.

14. The device of claim 9, wherein said locking portion includes a locking element movable with respect to said body portion, and said actuator is coupled to said locking element of said locking portion.

15. A system for adjusting tension in an artificial chordae tendineae, the system comprising:
- a clip engageable with a leaflet of a heart valve;
- an anchor engageable with a papillary muscle or heart wall; and
- an artificial chordae tendineae disposed between the clip and the anchor;
- wherein the anchor includes:
  - a body portion, and
  - a locking portion engageable with the artificial chordae tendineae and configured to allow movement of the artificial chordae tendineae with respect to the body portion;
- wherein the system further comprises an actuator coupled to the locking portion;

wherein the actuator is configured to shift the locking portion between an unlocked configuration where the artificial chordae is movable relative to the body portion and a locked configuration where the artificial chordae is substantially fixed relative to the body portion; and wherein the actuator extends proximally to a user so that the user can activate the actuator by pulling the actuator.

* * * * *